United States Patent
Wall et al.

(10) Patent No.: US 8,808,666 B2
(45) Date of Patent: Aug. 19, 2014

(54) PEPTIDES THAT SPECIFICALLY TARGET AMYLOID DEPOSITS

(71) Applicant: University of Tennessee Research Foundation, Knoxville, TN (US)

(72) Inventors: Jonathan Wall, Knoxville, TN (US); Stephen J. Kennel, Kingston, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 13/627,138

(22) Filed: Sep. 26, 2012

(65) Prior Publication Data

US 2013/0022546 A1 Jan. 24, 2013

Related U.S. Application Data

(63) Continuation-in-part of application No. PCT/US2011/029430, filed on Mar. 22, 2011.

(60) Provisional application No. 61/318,083, filed on Mar. 26, 2010.

(51) Int. Cl.
  *C07K 14/435* (2006.01)
  *G01N 33/566* (2006.01)
  *A61K 49/00* (2006.01)
  *C07K 19/00* (2006.01)

(52) U.S. Cl.
  USPC ............ 424/9.1; 530/324; 530/326; 530/325; 435/7.1

(58) Field of Classification Search
  None
  See application file for complete search history.

(56) References Cited

U.S. PATENT DOCUMENTS

2007/0093415 A1* 4/2007 Martin ........................... 514/12

OTHER PUBLICATIONS

Kang, Identification of peptides that specifically bind AB1-40 amyloid in vitro and amyloid plaques in Alzheimer's disease brain using phage display, Neurobiology of Disease 14:146-156, 2003.*
Nordberg, Chronic nicotine treatment reduces b-amyloidosis in the brain of a mouse model of Alzheimer's disease (APPsw), Journal of Neurochemistry, 2002, 81, 655-658.*
Alape-Giron, 1998, sequence downloaded from the internet at address http://www.ncbi.nlm.nih.gov/protein/7434999?report=genbank &log$=protalign&blastrank=10 &RID=V4EX6JAY015.*
PBS, The Reptiles: Snakes, Feb. 2003.*
Jayaraman, C.W. et al., "Binding of a de novo Designed Peptide to Specific Glycosaminoglycans," FEBS Letters 482, 2000, pp. 154-158.
Rullo, Anthony et al., "Importance of the Spatial Display of Charged Residues in Heparin-Peptide Interactions," Biopolymers, 2010, vol. 93, No. 3, pp. 290-298. (online 2009).

* cited by examiner

*Primary Examiner* — Karlheinz R Skowronek
*Assistant Examiner* — Schuyler Milton
(74) *Attorney, Agent, or Firm* — Ian J. Griswold; Johnson, Marcou & Isaacs, LLC

(57) ABSTRACT

The present invention provides a novel method of detecting amyloids in a subject. The present invention provides peptides that bind selectively to amyloids and are useful for detecting amyloids and diagnosing and/or monitoring the progression of amyloid mediated conditions.

15 Claims, 14 Drawing Sheets

Figure 1
λ Immunoglobulin light chain Amyloidosis (ALλ): *pancreas*
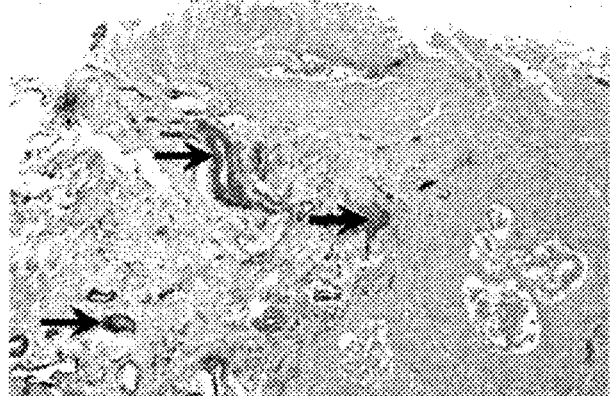
A
λ Immunoglobulin light chain Amyloidosis (ALλ): *thyroid*
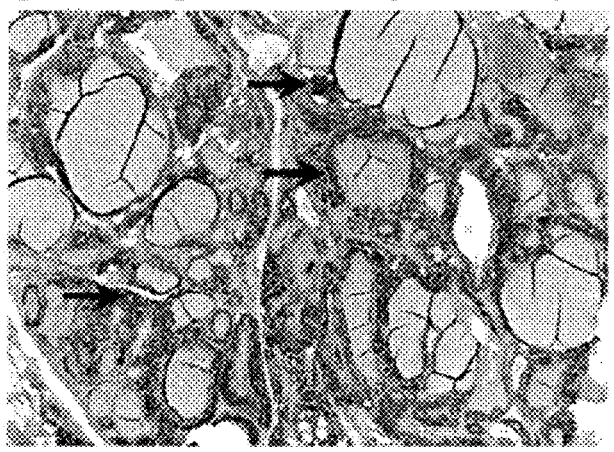
B
λ Immunoglobulin light chain Amyloidosis (ALλ): *kidney*
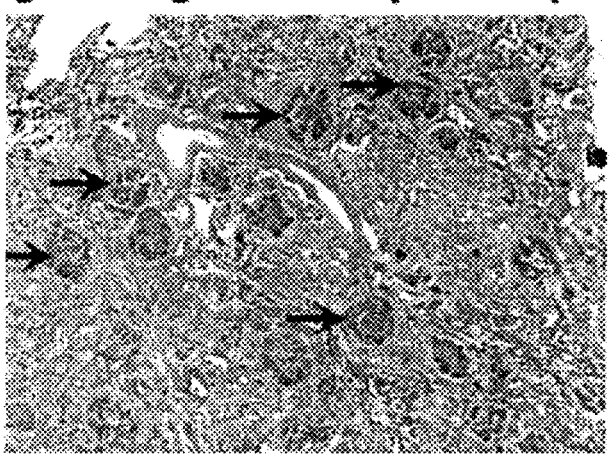
C

Figure 1
κ Immunoglobulin light chain Amyloidosis (ALκ)
*Heart*
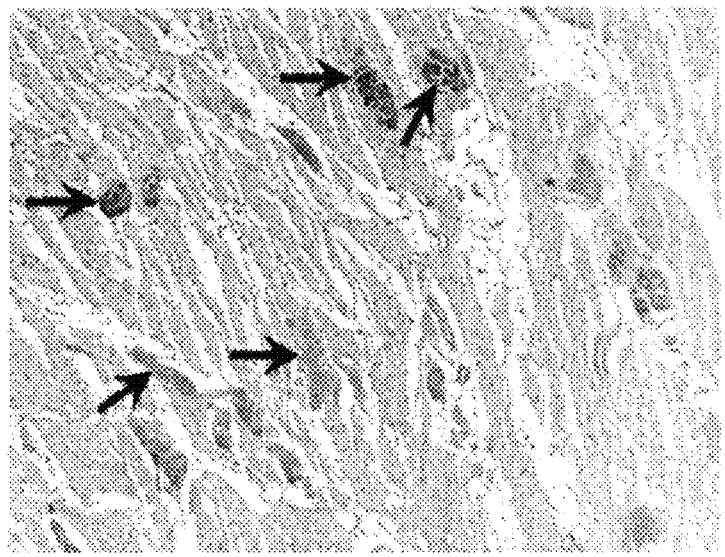
D
κ Immunoglobulin light chain Amyloidosis (ALκ)
*Liver*
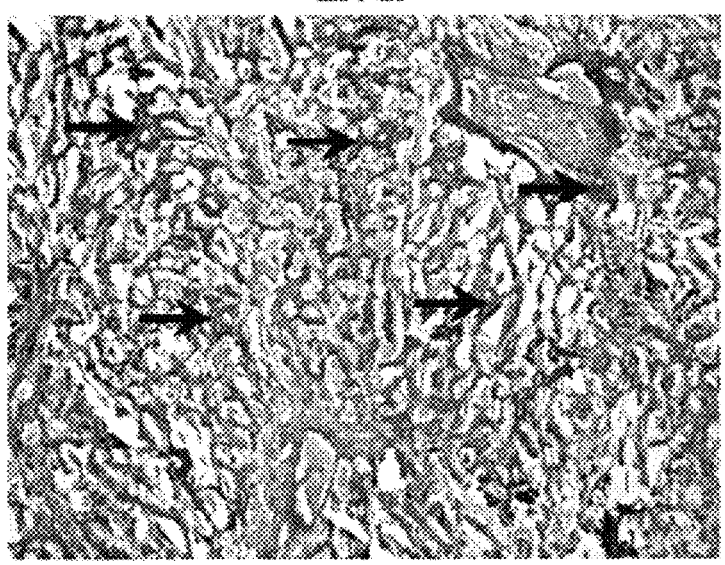
E

Figure 1
Transthyretin amyloidosis (ATTR)
F
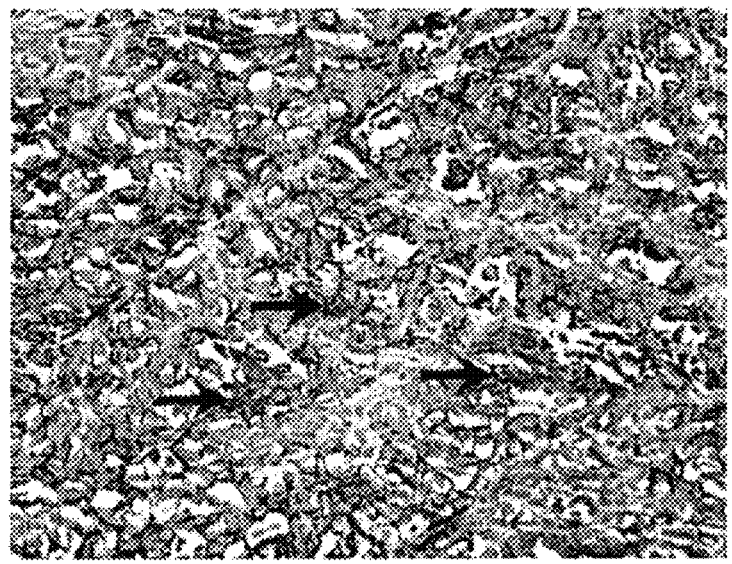
Serum amyloid protein A amyloidosis (AA)
G
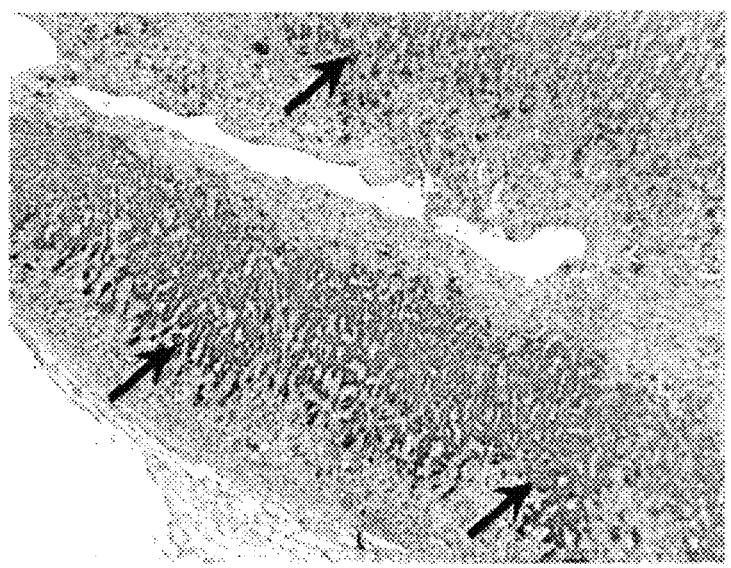

Figure 1
Calcifying epethilium odontogenic tumor amyloidosis (AODAM)
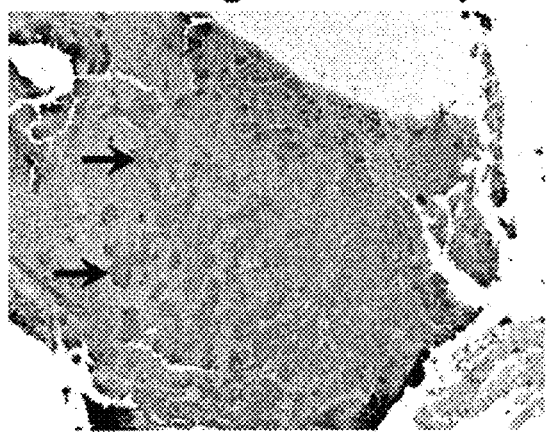
H
LecT 2 Amyloidosis (ALEC)
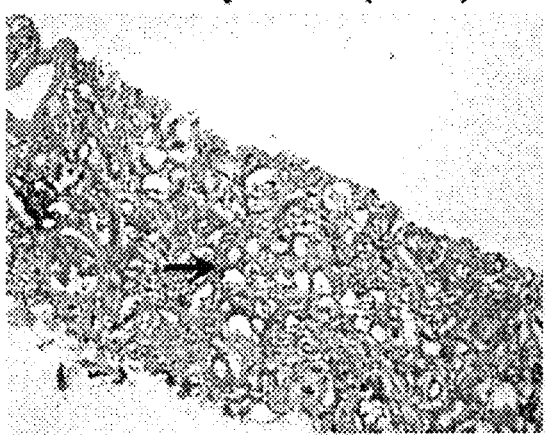
I
Galectin 7 Amyloidosis (AGal)
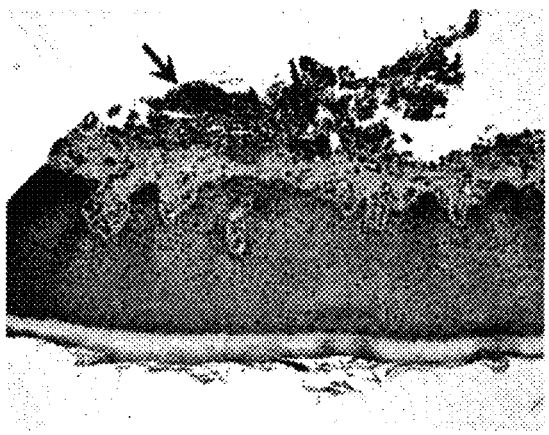
J

Figure 1
Amyloid beta Amyloidosis – Alzheimer's disease (Abeta)
K
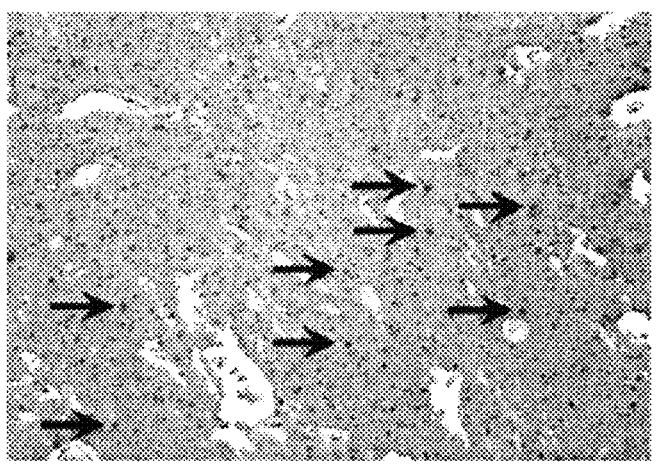
L
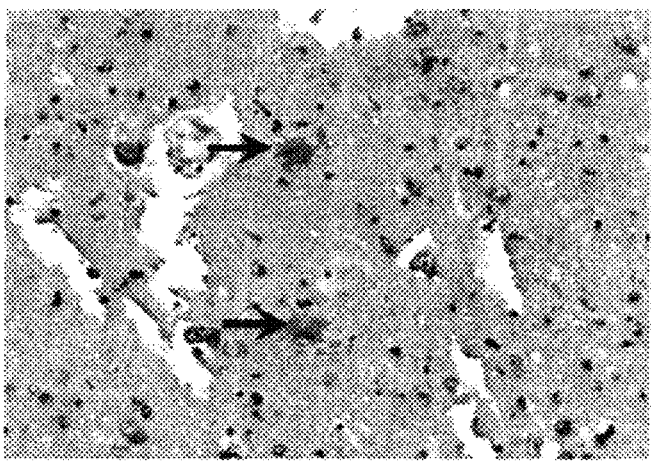
M
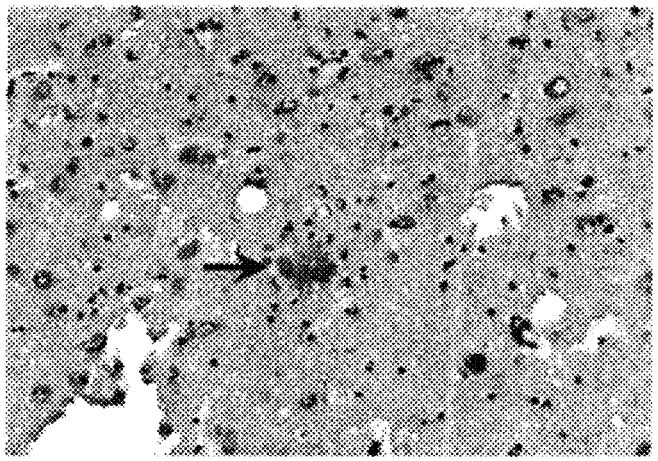

Figure 2
$^{125}$I-labeled peptide p31 SPECT imaging
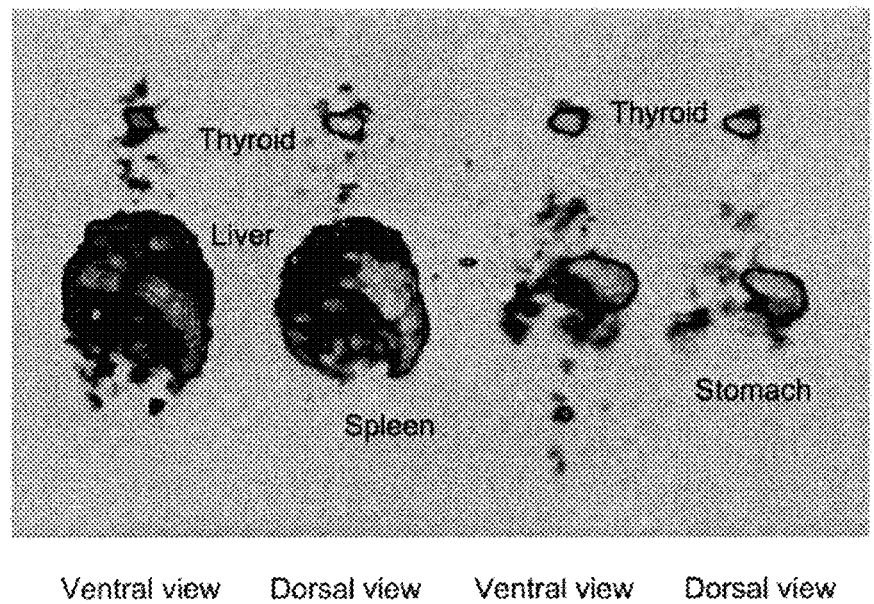
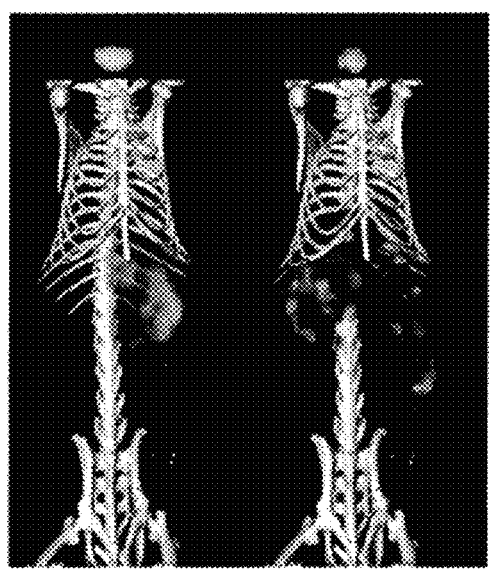

125I-labeled peptide p31 autoradiography 125I-labeled peptide p31 autoradiography 125I-labeled fusion p31 peptide SPECT imaging

SEQUENCE LISTING

```
<160> NUMBER OF SEQ ID NOS: 32

<210> SEQ ID NO 1
<211> LENGTH: 27
<212> TYPE: PRT
<213> ORGANISM: Artificial sequence
<220> FEATURE:
<223> OTHER INFORMATION: Binding Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
```

```
<400> SEQUENCE: 1

Xaa Asx Xaa Xaa Asx Xaa Xaa Xaa Asx Xaa Xaa Asx Xaa Xaa Xaa Asx
1               5                   10                  15

Xaa Xaa Asx Xaa Xaa Xaa Asx Xaa Xaa Asx Xaa
            20                  25

<210> SEQ ID NO 2
<211> LENGTH: 26
<212> TYPE: PRT
<213> ORGANISM: Artificial sequence
<220> FEATURE:
<223> OTHER INFORMATION: Binding Peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 2

Asx Xaa Glx Asx Xaa Glx Xaa Asx Glx Xaa Asx Glx Xaa Glx Asx Xaa
1               5                   10                  15

Glx Asx Xaa Glx Xaa Asx Glx Xaa Asx Glx
            20                  25

<210> SEQ ID NO 3
<211> LENGTH: 27
<212> TYPE: PRT
<213> ORGANISM: Artificial sequence
<220> FEATURE:
<223> OTHER INFORMATION: Heparin-binding peptide

<400> SEQUENCE: 3

Ser Arg Ala Gln Arg Ala Gln Ala Arg Gln Ala Arg Gln Ala Gln Arg
1               5                   10                  15

Ala Gln Arg Ala Gln Ala Arg Gln Ala Arg Gln
            20                  25

<210> SEQ ID NO 4
<211> LENGTH: 31
```

```
<212> TYPE: PRT
<213> ORGANISM: Artificial sequence
<220> FEATURE:
<223> OTHER INFORMATION: Heparin-binding peptide

<400> SEQUENCE: 4

Cys Gly Gly Tyr Ser Arg Ala Gln Arg Ala Gln Ala Arg Gln Ala Arg
1               5                   10                  15

Gln Ala Gln Arg Ala Gln Arg Ala Gln Ala Arg Gln Ala Arg Gln
            20                  25                  30

<210> SEQ ID NO 5
<211> LENGTH: 18
<212> TYPE: PRT
<213> ORGANISM: Homo sapiens

<400> SEQUENCE: 5

Cys Gly Gly Tyr Ser Arg Pro Arg Ala Arg Ala Arg Ala Arg Asp Gln
1               5                   10                  15

Thr Arg

<210> SEQ ID NO 6
<211> LENGTH: 31
<212> TYPE: PRT
<213> ORGANISM: Artificial sequence
<220> FEATURE:
<223> OTHER INFORMATION: Heparin-binding peptide

<400> SEQUENCE: 6

Cys Gly Gly Tyr Ser Lys Ala Gln Lys Ala Gln Ala Lys Gln Ala Lys
1               5                   10                  15

Gln Ala Gln Lys Ala Gln Lys Ala Gln Ala Lys Gln Ala Lys Gln
            20                  25                  30

<210> SEQ ID NO 7
<211> LENGTH: 26
<212> TYPE: PRT
<213> ORGANISM: Oncorhynchus tshawytscha

<400> SEQUENCE: 7

Cys Gly Gly Tyr Pro Arg Arg Arg Arg Ser Ser Arg Pro Ile Arg
1               5                   10                  15

Arg Arg Arg Pro Arg Arg Ala Ser Arg Arg
            20                  25

<210> SEQ ID NO 8
<211> LENGTH: 36
<212> TYPE: PRT
<213> ORGANISM: Artificial sequence
<220> FEATURE:
<223> OTHER INFORMATION: Heparin-binding peptide

<400> SEQUENCE: 8

Cys Gly Gly Tyr Ala Arg Lys Lys Ala Ala Lys Ala Ala Arg Lys Lys
1               5                   10                  15

Ala Ala Lys Ala Ala Arg Lys Lys Ala Ala Lys Ala Val Leu Val Leu
            20                  25                  30

Val Leu Val Leu
        35

<210> SEQ ID NO 9
<211> LENGTH: 21
<212> TYPE: PRT
```

```
<213> ORGANISM: Homo sapiens

<400> SEQUENCE: 9

Cys Gly Gly Tyr Phe Ala Lys Leu Asn Cys Arg Leu Tyr Arg Lys Ala
1               5                   10                  15

Asn Lys Ser Ser Lys
            20

<210> SEQ ID NO 10
<211> LENGTH: 30
<212> TYPE: PRT
<213> ORGANISM: Oncorhynchus mykiss

<400> SEQUENCE: 10

Cys Gly Gly Tyr Ser Ser Arg Pro Val Arg Arg Arg Arg Pro
1               5                   10                  15

Arg Val Ser Arg Arg Arg Arg Gly Gly Arg Arg Arg Arg
            20                  25                  30

<210> SEQ ID NO 11
<211> LENGTH: 30
<212> TYPE: PRT
<213> ORGANISM: Plasmodium vivax

<400> SEQUENCE: 11

Cys Gly Gly Tyr Gly Asp Ala Lys Lys Lys Asp Gly Lys Lys Ala
1               5                   10                  15

Glu Pro Lys Asn Pro Arg Glu Asn Lys Leu Lys Gln Pro Gly
            20                  25                  30

<210> SEQ ID NO 12
<211> LENGTH: 24
<212> TYPE: PRT
<213> ORGANISM: Homo sapiens

<400> SEQUENCE: 12

Cys Gly Gly Tyr Pro Lys Lys Gly Ser Lys Lys Ala Val Thr Lys Ala
1               5                   10                  15

Gln Lys Lys Asp Gly Lys Lys Arg
            20

<210> SEQ ID NO 13
<211> LENGTH: 31
<212> TYPE: PRT
<213> ORGANISM: Artificial Sequence
<220> FEATURE:
<223> OTHER INFORMATION: Synthetic

<400> SEQUENCE: 13

Gly Gly Gly Tyr Ser Lys Ala Gln Lys Ala Gln Ala Lys Gln Ala Lys
1               5                   10                  15

Gln Ala Gln Lys Ala Gln Lys Ala Gln Ala Lys Gln Ala Lys Gln
            20                  25                  30

<210> SEQ ID NO 14
<211> LENGTH: 45
<212> TYPE: PRT
<213> ORGANISM: Artificial Sequence
<220> FEATURE:
<223> OTHER INFORMATION: Synthetic

<400> SEQUENCE: 14

Cys Gly Gly Tyr Ser Lys Ala Gln Lys Ala Gln Ala Lys Gln Ala Lys
```

```
1               5                   10                  15
Gln Ala Gln Lys Ala Gln Lys Ala Gln Ala Lys Gln Ala Lys Gln Ala
                20                  25                  30
Gln Lys Ala Gln Lys Ala Gln Ala Lys Gln Ala Lys Gln
        35                  40                  45
```

<210> SEQ ID NO 15
<211> LENGTH: 41
<212> TYPE: PRT
<213> ORGANISM: Artificial Sequence
<220> FEATURE:
<223> OTHER INFORMATION: Synthetic

<400> SEQUENCE: 15

```
Arg Arg Leu Ser Tyr Ser Arg Arg Phe Cys Gly Gly Tyr Ser Lys
1               5                   10                  15
Ala Gln Lys Ala Gln Ala Lys Gln Ala Lys Gln Ala Gln Lys Ala Gln
                20                  25                  30
Lys Ala Gln Ala Lys Gln Ala Lys Gln
        35                  40
```

<210> SEQ ID NO 16
<211> LENGTH: 42
<212> TYPE: PRT
<213> ORGANISM: Artificial Sequence
<220> FEATURE:
<223> OTHER INFORMATION: Synthetic

<400> SEQUENCE: 16

```
Tyr Gly Arg Lys Lys Arg Arg Gln Arg Arg Cys Gly Gly Tyr Ser
1               5                   10                  15
Lys Ala Gln Lys Ala Gln Ala Lys Gln Ala Lys Gln Ala Gln Lys Ala
                20                  25                  30
Gln Lys Ala Gln Ala Lys Gln Ala Lys Gln
        35                  40
```

<210> SEQ ID NO 17
<211> LENGTH: 24
<212> TYPE: PRT
<213> ORGANISM: Artificial Sequence
<220> FEATURE:
<223> OTHER INFORMATION: Synthetic

<400> SEQUENCE: 17

```
Cys Gly Gly Tyr Ser Lys Ala Gln Lys Ala Gln Ala Lys Gln Ala Lys
1               5                   10                  15
Gln Ala Gln Lys Ala Gln Lys Ala
                20
```

<210> SEQ ID NO 18
<211> LENGTH: 49
<212> TYPE: PRT
<213> ORGANISM: Artificial Sequence
<220> FEATURE:
<223> OTHER INFORMATION: Synthetic

<400> SEQUENCE: 18

```
Thr Phe Phe Tyr Gly Gly Ser Arg Gly Lys Arg Asn Asn Phe Lys Thr
1               5                   10                  15
Glu Glu Tyr Gly Gly Tyr Ser Lys Ala Gln Lys Ala Gln Ala Lys Gln
                20                  25                  30
Ala Lys Gln Ala Gln Lys Ala Gln Lys Ala Gln Ala Lys Gln Ala Lys
```

Gln

<210> SEQ ID NO 19
<211> LENGTH: 51
<212> TYPE: PRT
<213> ORGANISM: Artificial Sequence
<220> FEATURE:
<223> OTHER INFORMATION: Synthetic

<400> SEQUENCE: 19

Gly Gly Tyr Ser Lys Ala Gln Lys Ala Gln Ala Lys Gln Ala Lys Gln
1               5                   10                  15

Ala Gln Lys Ala Gln Lys Ala Gln Ala Lys Gln Ala Lys Gln Gly Gly
            20                  25                  30

Thr Phe Phe Tyr Gly Gly Ser Arg Gly Lys Arg Asn Asn Phe Lys Thr
        35                  40                  45

Glu Glu Tyr
    50

<210> SEQ ID NO 20
<211> LENGTH: 45
<212> TYPE: PRT
<213> ORGANISM: Artificial Sequence
<220> FEATURE:
<223> OTHER INFORMATION: Synthetic

<400> SEQUENCE: 20

Gly Gly Gly Tyr Ser Lys Ala Gln Lys Ala Gln Ala Lys Gln Ala Lys
1               5                   10                  15

Gln Ala Gln Lys Ala Gln Lys Ala Gln Ala Lys Gln Ala Lys Gln Ala
            20                  25                  30

Gln Lys Ala Gln Lys Ala Gln Ala Lys Gln Ala Lys Gln
        35                  40                  45

<210> SEQ ID NO 21
<211> LENGTH: 45
<212> TYPE: PRT
<213> ORGANISM: Artificial Sequence
<220> FEATURE:
<223> OTHER INFORMATION: Synthetic

<400> SEQUENCE: 21

Cys Gly Gly Tyr Ser Arg Ala Gln Arg Ala Gln Ala Arg Gln Ala Arg
1               5                   10                  15

Gln Ala Gln Arg Ala Gln Arg Ala Gln Ala Arg Gln Ala Arg Gln Ala
            20                  25                  30

Gln Arg Ala Gln Arg Ala Gln Ala Arg Gln Ala Arg Gln
        35                  40                  45

<210> SEQ ID NO 22
<211> LENGTH: 31
<212> TYPE: PRT
<213> ORGANISM: Artificial Sequence
<220> FEATURE:
<223> OTHER INFORMATION: Synthetic

<400> SEQUENCE: 22

Gly Gly Gly Tyr Ser Arg Ala Gln Arg Ala Gln Ala Arg Gln Ala Arg
1               5                   10                  15

Gln Ala Gln Arg Ala Gln Arg Ala Gln Ala Arg Gln Ala Arg Gln
            20                  25                  30

<210> SEQ ID NO 23
<211> LENGTH: 18
<212> TYPE: PRT
<213> ORGANISM: Artificial Sequence
<220> FEATURE:
<223> OTHER INFORMATION: Synthetic

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 16
<212> TYPE: PRT
<213> ORGANISM: Drosophila

<400> SEQUENCE: 24

Arg Gln Ile Lys Ile Trp Phe Gln Asn Arg Arg Met Lys Trp Lys Lys
1               5                   10                  15

<210> SEQ ID NO 25
<211> LENGTH: 27
<212> TYPE: PRT
<213> ORGANISM: Vespula lewisii
<220> FEATURE:
<221> NAME/KEY: misc_feature
<223> OTHER INFORMATION: Wasp Venom

<400> SEQUENCE: 25

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 26
<211> LENGTH: 27
<212> TYPE: PRT
<213> ORGANISM: SV40 virus

<400> SEQUENCE: 26

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 27
<211> LENGTH: 27
<212> TYPE: PRT
<213> ORGANISM: SV40 virus

<400> SEQUENCE: 27

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 28
<211> LENGTH: 13
<212> TYPE: PRT
<213> ORGANISM: HIV

<400> SEQUENCE: 28

```
Gly Arg Lys Lys Arg Gln Arg Arg Pro Pro Gln
1               5                  10
```

```
<210> SEQ ID NO 29
<211> LENGTH: 18
<212> TYPE: PRT
<213> ORGANISM: Unknown
<220> FEATURE:
<223> OTHER INFORMATION: Mammalian Leukocyte

<400> SEQUENCE: 29

Arg Gly Gly Arg Leu Ser Tyr Ser Arg Arg Phe Ser Thr Ser Thr
1               5                   10                  15

Gly Arg
```

```
<210> SEQ ID NO 30
<211> LENGTH: 9
<212> TYPE: PRT
<213> ORGANISM: Unknown
<220> FEATURE:
<223> OTHER INFORMATION: Mammalian Leukocyte

<400> SEQUENCE: 30

Arg Arg Leu Ser Tyr Ser Arg Arg Phe
1               5
```

```
<210> SEQ ID NO 31
<211> LENGTH: 19
<212> TYPE: PRT
<213> ORGANISM: Artificial Sequence
<220> FEATURE:
<223> OTHER INFORMATION: Synthetic

<400> SEQUENCE: 31

Thr Phe Phe Tyr Gly Gly Ser Arg Gly Lys Arg Asn Asn Phe Lys Thr
1               5                   10                  15

Glu Glu Tyr
```

```
<210> SEQ ID NO 32
<211> LENGTH: 45
<212> TYPE: PRT
<213> ORGANISM: Artificial Sequence
<220> FEATURE:
<223> OTHER INFORMATION: Synthetic peptide

<400> SEQUENCE: 32

Gly Gly Gly Tyr Ser Arg Ala Gln Arg Ala Gln Ala Arg Gln Ala Arg
1               5                   10                  15

Gln Ala Gln Arg Ala Gln Arg Ala Gln Ala Arg Gln Ala Arg Gln Ala
                20                  25                  30

Gln Arg Ala Gln Arg Ala Gln Ala Arg Gln Ala Arg Ala
            35                  40                  45
```

PEPTIDES THAT SPECIFICALLY TARGET AMYLOID DEPOSITS

RELATED APPLICATIONS

This application is a continuation-in-part of International Application No. PCT/US2011/029430 filed Mar. 22, 2011 and claims the benefit of U.S. Provisional Application 61/318,083, filed on Mar. 26, 2010, both of which are incorporated by reference herein in their entirety.

FEDERAL SUPPORT

This invention was made with United States government support under National Institutes of Health (NIDDK) contract DK079984. The United States government has certain rights in the invention.

FIELD OF THE INVENTION

The present invention relates to a class of peptides that bind to amyloid deposits. These peptides may be used as tools for diagnosing amyloidosis.

BACKGROUND OF THE INVENTION

Amyloidosis is a fatal protein-folding disorder characterized by the aggregation and deposition of proteinaceous fibrils and heparan sulfate proteoglycan in vital organs and tissues (Merlini, G. et al. (2003) N. Engl. J. Med. 349, 583-596; Merlini, G. et al. (2004) J. Intern. Med. 255, 159-178; De Lorenzi, E. et al. (2004) Curr. Med. Chem. 11, 1065-1084; Merlini, G. (2004) Neth. J. Med. 62, 104-105). The unrelenting accumulation of amyloid invariably leads to organ dysfunction and severe morbidity or death. The deposits can be cerebral, as in patients with Alzheimer's, Huntington's or prion diseases, or peripheral such as seen in patients with light chain (AL) amyloidosis and type 2 diabetes. Further subgrouping into localized or systemic indicates whether the precursor protein is produced locally (at the site of deposition) or circulates in the blood stream, respectively (Westermark, P. et al. (2007) Amyloid. 14, 179-183). Amyloid can affect any organ or tissue but the kidneys, pancreas, liver, spleen, nervous tissue and heart constitute the major sites of deposition in patients with familial or sporadic forms of peripheral amyloid disease. Alzheimer's disease currently affects more than 4 million Americans and this figure is estimated to increase to more than 16 million by the year 2050. It is by far the most common form of amyloidosis and poses the greatest socioeconomic impact. In contrast, the peripheral amyloidoses are orphan disorders but account for more than 5,000 new patients annually in the USA alone.

Of these, the major peripheral amyloidosis is AL, a sporadic monoclonal plasma cell dyscrasia resulting in the deposition of fibrils composed of immunoglobulin light chain proteins. AL accounts for approximately two thirds of all peripheral amyloid cases and has a calculated incidence of ~1.4 per 100,000 persons per year in the USA, which is comparable to that of acute lymphocytic and chronic myeloid leukemias (Group, U.S.C. S. W. (2007) United States Cancer Statistics: 1999-2003 Incidence and Mortality Web-Based Report, U.S. Department of Health and Human Services Centers for Disease Control and Prevention National Cancer Institute, Atlanta). Although AL is one fifth as common as the related plasma cell dyscrasia multiple myeloma it is arguably more devastating with a median survival of only 13.2 months due partly to the rapidly progressive nature of the organ destruction, the lack of effective anti-amyloid therapeutics and the inability to effectively diagnose the disease before organ failure occurs. Fewer than 5% of all AL patients survive 10 years or more from the time of diagnosis (Comenzo, R. L. et al. (2002) Blood 99, 4276-4282). Moreover, in patients with cardiac AL amyloidosis the median survival is less than 5 months. Unfortunately, there is no effective mouse model of AL disease.

The second most prevalent form of peripheral amyloidosis in this country is (AA) amyloidosis which is associated with chronic inflammatory disorders such as arthritis, tuberculosis and Familial Mediterranean Fever. The incidence of AA is even greater in certain regions of Europe than in the US and the frequency varies among ethnic groups (Buck, F. S. et al. (1989) Mod. Pathol. 2, 372-377). In areas where Familial Mediterranean Fever is prevalent and goes untreated, the incidence of AA can be 100%. However, in Europe the incidence, based on autopsy studies performed in the Denmark, is estimated to be 0.86% (Lofberg, H. et al. (1987) Acta pathologica, microbiologica, et immunologica Scandinavica 95, 297-302); however, in patients with rheumatoid or psoriatic arthritis the occurrence of AA can be as high as 26%. Such a high prevalence may warrant a screening program to detect the disease earlier. Deposition of amyloid is associated with a sustained increase in the plasma concentration of serum amyloid (sAA) protein A, the precursor of the amyloid fibrils (Rocken, C. et al. (2002) Virchows Arch. 440, 111-122). AA differs from AL in the type of precursor protein that is deposited but both share common mechanistic features associated with fibril formation and deposition (Rocken, C. et al. (2006) J. Pathol. 210, 478-487; Rocken, C. et al. (2001) Am. J. Pathol. 158, 1029-1038).

In addition to the disorders in which the etiopathology of amyloid is well established, fibrillar deposits with the structural and tinctorial properties of amyloid have been identified in other syndromes although their relevance to the disease state has yet to be established. In type 2 diabetes for example, islet amyloid precursor protein (IAPP) deposits as amyloid in the Islets of Langerhans (Jaikaran, E. T. et al. (2001) Biochim. Biophys. Acta 1537, 179-203). The aggregation of IAPP results in oligomeric structures that are toxic to pancreatic cells (Lin, C. Y. et al. (2007) Diabetes 56, 1324-1332). Thus, it is suggested that the formation of IAPP amyloid in type 1 diabetic patients contributes to β cell destruction and ushers in the transition to insulin dependence (Jaikaran, E. T. et al. (2001) Biochim. Biophys. Acta 1537, 179-203). In another example, plaques containing amyloid fibrils composed of apolipoprotein A-I have been identified in over half of patients with atherosclerotic carotid arteries (Westermark, P. et al. (1995) Am. J. Pathol. 147, 1186-1192; Mucchiano, G. I. et al. (2001) J. Pathol. 193, 270-275). The deposition of these fibrils was more common in older patients but apoA-I is undoubtedly present early in plaque development (Vollmer, E. et al. (1991) Virchows Arch. A. Pathol. Anat. Histopathol. 419, 79-88). As a final example, Apo-A-I amyloid was also recently identified in knee joint menisci obtained from patients having knee replacement surgery and may contribute to the physical deterioration of the joint (Solomon, A. et al. (2006) Arthritis Rheum. 54, 3545-3550).

In total more than 25 proteins have been chemically or serologically identified as constituents of fibrils in amyloid deposits. It is the nature of these proteins that differentiate the diseases, determine the treatment, and establish the prognosis. Although amyloid fibrils are associated with a clinically heterogeneous group of diseases and can form from structurally distinct and functionally diverse precursor proteins, the deposits themselves share a number of remarkably similar characteristics including fibril structure, fibril epitopes and accrual of similar accessory molecules including heparan sulfate proteoglycans (HSPGs). Amyloid is a heterogeneous complex that includes, in addition to fibrils, glycosaminoglycans (GAGs) and in particular the perlecan HSPG (Ancsin, J. B. (2003) Amyloid 10, 67-79; Ailles, L. et al. (1993) Lab. Invest. 69, 443-448; Kisilevsky, R. (1994) Mol. Neurobiol. 9, 23-24; Kisilevsky, R. (1990) Lab. Invest. 63, 589-591; Snow, A. D. et al. (1987) Lab. Invest. 56, 120-123; Li, J. P. et al. (2005) Proc. Natl. Acad. Sci. USA 102, 6473-6477).

One problem that is encountered in the field of therapy of amyloid-related disorders is the inability to quantitatively and at high resolution image amyloid in a patient suffering therefrom. To date, no satisfactory method has been developed by which it is possible to obtain a rapid quantitative, whole-body tomographic image of amyloid deposition in a patient. Consequently, it is difficult, if even possible, to accurately monitor response to therapy for amyloidosis in a live subject. Instead, post-mortem analysis of the extent of amyloid is currently the means by which response to therapy for amyloidosis is evaluated, or by using surrogate markers of organ function which are presumed to be an indirect measure of amyloid burden. A significant need exists for a method by which an ante-mortem determination of the degree and extent of amyloidosis may be obtained. Such a method would permit the assessment of the extent of amyloidosis in an individual which can aid in the diagnosis of the disease, assist in determining the prognosis, define the therapeutic options, and enable the rational evaluation of therapeutic response of novel anti-amyloid therapeutics.

SUMMARY OF THE INVENTION

The present invention provides isolated peptides that bind amyloid deposits, wherein the peptide has an amino acid sequence consisting of at least 3 amino acids to at most 55 amino acids. The peptide may have an amino acid sequence consisting of at least 10 amino acids, at least 15 amino acids, at least 20 amino acids, at least 25 amino acids, at least 30 amino acids, at least 35 amino acids, at least 40 amino acids, at least 45 amino acids, or at least 50 amino acids and at most 55 amino acids. The peptide may consists of 18 amino acids, 21 amino acids, 24 amino acids, 26 amino acids, 30 amino acids, 31 amino acids, 36 amino acids, 41 amino acids, 42 amino acids, 45 amino acids, 49 amino acids, or 51 amino acids.

The peptide of the present invention may have an amino acid sequence comprising at least 15% positively charged amino acids. The positively charged amino acids may be arginine, lysine, histidine or a combination thereof. The peptide may comprise an amino acid sequence as set forth in any one of SEQ ID NOs: 1 through 22, and 32 and consist of at most 55 amino acids. The peptide may comprise an amino acid sequence as set forth in any one or SEQ ID NOs: 1 through 22 and 32. Alternatively, the peptide may consist of an amino acid sequence as set forth in SEQ ID NO: 32, SEQ ID NO: 1, SEQ ID NO: 2, SEQ ID NO: 3, SEQ ID NO: 4, SEQ ID NO: 13, SEQ ID NO: 14, SEQ ID NO: 20, SEQ ID NO: 21, or SEQ ID NO: 22.

The present invention also provides a fusion peptide comprising the peptide of the present invention fused to a second peptide, which may be fused to the amino terminus or carboxy terminus of the first peptide, the peptide that binds amyloid. The second peptide may be fused to the amino terminus of the peptide for ease of labeling the peptide for detection. The second peptide may have the sequence CGGY (amino acids 1 to 4 of SEQ ID NO: 4) or GGGY (amino acids 1 to 4 of SEQ ID NO: 13). The fusion peptide may contain an imaging agent.

The fusion protein of the present invention may also comprise a first peptide of the present invention which binds amyloids and a second peptide which may be a cell penetrating peptide or a blood brain barrier translocating peptide.

The present invention provides a pharmaceutical composition comprising one or more peptides of the present invention, one or more fusion proteins of the present invention, or a combination thereof.

The present invention provides methods of using the peptides of the present invention to detect amyloids. In one embodiment, the present invention provides a method of detecting amyloids in a subject comprising administering to a subject a pharmaceutical composition of the present invention and detecting the presence of amyloids in the subject. The amyloids may be detected by imaging the subject.

In another embodiment, the present invention provides a method of diagnosing amyloidosis in a subject comprising administering to a subject a pharmaceutical composition of the present invention and detecting the presence of amyloids in the subject, wherein the presence of amyloids indicates that the subject is suffering from amyloidosis.

The present invention also provides a method of monitoring progression of amyloidosis in a subject comprising administering to a subject a pharmaceutical composition of the present invention detecting the presence of amyloid fibrils in the subject, thereby monitoring the progression of amyloidosis in the subject. The method of the present invention may be used to monitor the response of a subject diagnosed with amyloidosis to a therapeutic agent comprising administering to a subject who has been treated or is being treated with a therapeutic agent, a pharmaceutical composition of the present invention, and detecting the presence of amyloids in the subject, thereby monitoring the response of the subject to the therapeutic agent.

The present invention also provides a method of monitoring the efficacy of an anti-amyloid therapy in a subject comprising administering to a subject undergoing anti-amyloid therapy a pharmaceutical composition of the present invention and detecting the presence of amyloid fibrils in the subject, thereby monitoring the efficacy of the anti-amyloid therapy in the subject.

The images obtained by the methods of the present invention may be compared with images obtained with a control subject or a control reagent. The control subject may be a healthy subject. The control reagent may be a known reagent that binds amyloid such as serum amyloid P component (SAP). Also, a recently obtained image may be compared to an image obtained previously, such as an image obtained prior to the commencement of anti-amyloid therapy or treatment with therapeutic agent, or an image obtained any time prior to the recently obtained image.

The present invention also provides a method of detecting amyloids in tissue samples from a subject. The present invention also provides a method of diagnosing amyloidosis, monitoring the progression of amyloidosis, and monitoring the efficacy of an anti-amyloid therapy in a subject using a tissue sample.

The method comprises obtaining a tissue sample from a subject, applying the peptide or fusion peptide to the tissue sample and detecting the binding of the peptide or fusion peptide to the amyloid. Detecting the presence of amyloids may involve visualizing the binding of the peptide or fusion peptide to the amyloid using fluorescence, or standard histochemical techniques. The method may further comprise obtaining tissue sections from the tissue samples and staining the tissue sections and detecting the presence of amyloids in the tissue samples by visualizing the binding of the peptide to the amyloid using fluorescence, or standard histochemical techniques.

The subject may be suffering from or diagnosed with an amyloid mediated condition. The subject may be suspected of having an amyloid mediated condition. The subject may be in need of treatment or diagnosis of an amyloid mediated condition. The subject may be in need of being monitored for progression, or monitored for the efficacy of an anti-amyloid therapy. Peptides or fusion peptides of the present invention may be administered to such subject. Alternatively, tissues samples may be obtained from such subject.

The present invention also provides kits comprising the peptide or fusion peptide of the present invention. The kits may further comprise labeling agent and/or means for detecting the binding of the peptide or fusion peptide to amyloids. The kit may be a tissue staining kit containing the reagents required for staining a tissue sample. The kit may be an imaging kit containing the reagents for imaging a subject or tissue.

BRIEF DESCRIPTION OF THE DRAWINGS

FIGS. 1A-M show immunohistochemical overlays of amyloid containing tissues. (A) λ Immunoglobulin light chain amyloidosis (ALλ): pancreas; (B) ALλ: thyroid; (C) ALλ: kidney; (D) κ Immunoglobulin light chain amyloidosis (ALκ): heart; (E) ALκ: liver; (F) Transthyretin amyloidosis (ATTR); (G) Serum amyloid protein A amyloidosis (AA); (H) Calcifying epithelium odontogenic tumor amyloidosis (AODAM); (I) LecT 2 amyloidosis (ALEC2); (J) Galectin 7 amyloidosis (AGal); (K, L, and M) Amyloid amyloidosis (Aβ)-Alzheimer's disease. Peptides selectively bound to the amyloid in the tissue section as evidenced by the arrows which coincides with amyloid seen histologically in consecutive tissue sections.

FIGS. 2A and B show $^{125}$I-labeled peptide p31 SPECT imaging. SPECT images of peptide p31 in mice with AA amyloid and control (healthy wild type (WT)) mice without amyloid. (A) AA mouse compared to WT mouse; (B) Fused images of AA mouse and WT mouse showing the difference between the distribution in the two animals. The distribution of peptide p31 is totally different in the AA mouse as compared to the control indicating that it is binding to amyloid and is a good imaging agent for this pathology in vivo.

DETAILED DESCRIPTION

Figure 3:
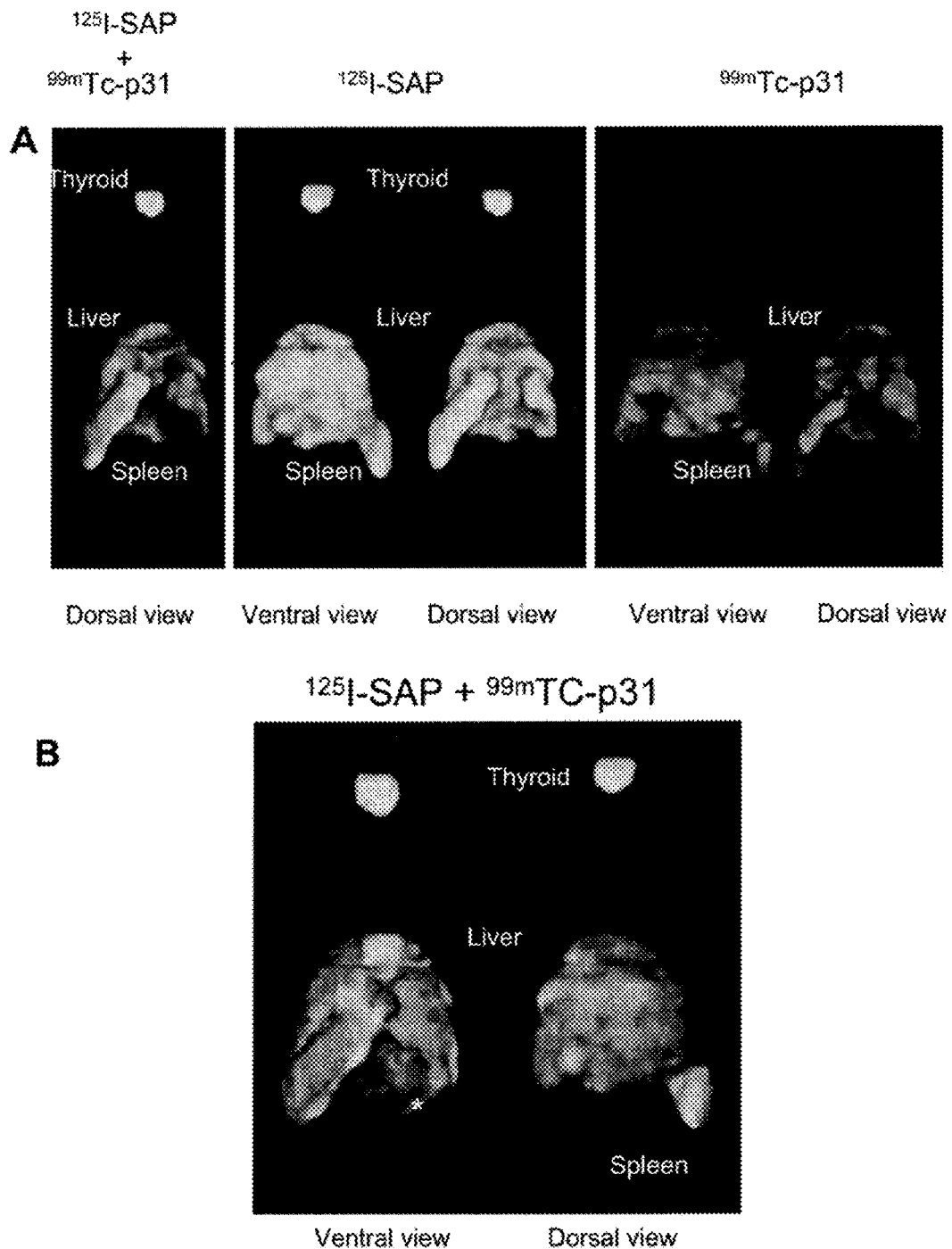
FIGS. 3A and B show $^{99m}$Tc-labeled peptide p31 SPECT imaging of AA amyloid in a single mouse. (A and B) SPECT images of serum amyloid P component (SAP) which is labeled green and peptide 31 which is labeled red are compared. SAP is the gold standard imaging for amyloid used clinically. The distribution of peptide p31 is the same as that for SAP indicating that it is as good as SAP at binding to an amyloid in vivo.

As used herein, an "amino acid" or "amino acid residue" refers to any naturally occurring amino acid, any non-naturally occurring amino acid, any modified including derivatized amino acid, or any amino acid mimetic known in the art. The amino acid may be referred by both their common three letter abbreviation and single letter abbreviation.

As used herein, the term "amyloids," "amyloid deposits," or "amyloid fibrils" refers to insoluble fibrous protein aggregates sharing specific structural traits. Abnormal accumulation of amyloids in organs may lead to amyloidosis. Although they are diverse in their occurrence, all amyloids have common morphologic properties such as stain with specific dyes such as Congo Red, and have a characteristic red-green birefringent appearance in polarized light after staining Amyloids also share common ultrastructural features and common x-ray diffraction and infrared spectra.

As used herein the term "amyloidosis" refers to a pathological condition or disease characterized by the presence of amyloids.

As used herein, the term "carriers" includes pharmaceutically acceptable carriers, excipients, or stabilizers which are nontoxic to the cell, tissue, mammal, or subject being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween®, polyethylene glycol (PEG), and Pluronics®.

As used herein, the term "effective amount" or "suitable amount" is an amount sufficient to effect beneficial or desired clinical or biochemical results. An effective amount can be administered one or more times. For purposes of this invention, an effective amount of a peptide or fusion peptide of the present invention is an amount that is sufficient to bind to and allow detection of the amyloids. A peptide or fusion peptide of the present invention is effective when parenterally administered in amounts above about 1 µg per kg of body weight to about 30 mg/kg.

As used herein, the term "imaging agent" or "contrast agent" which terms may be used interchangeably, refers to any agent which may be used in connection with methods for imaging an internal region of a subject and/or diagnosing the presence or absence of a disease in a subject by the application and/or detection of an energy source. Exemplary imaging agents include contrast agents for use in connection with ultrasound, magnetic resonance imaging, radionuclide imaging, or x-ray (including computed tomography) imaging of a patient, and the compositions described herein.

As used herein, the term "mammal" for purposes of the present invention refers to any animal classified as a mammal, including humans, domestic and farm animals, and zoo, sports, or pet animals, such as dogs, cats, cattle, horses, sheep, pigs, and so on. The mammal may be a human.

As used herein, the term "peptide" refers to any peptide or peptidomimetic structure comprising or consisting of two or more amino acids, including chemical modifications and derivatives of amino acids. The peptides of the present invention may comprise or consist of less than 55 amino acids.

As used herein, the term "purified" or "isolated" molecule refers to biological or synthetic molecules that are removed from their natural environment and are isolated or separated and are free from other components with which they are naturally associated.

As used herein, the term "specifically binds" refers to a non-random binding reaction between two molecules, for example between a peptide of the present invention and an amyloid. The term "specifically binds" may be used interchangeably with "selectively targets" or "selectively associates."

As used herein, the term "selectively targets" or "selectively associates" with reference to amyloids, refers to, for example, the selective localization or binding of a peptide of the present invention to an amyloid.

As used herein, the term "subject" refers to a vertebrate. The vertebrate may be a mammal, for example, a human. The subject may be a human patient. A subject may be a patient suffering from or suspected of suffering from a disease or condition and may be in need of treatment or diagnosis or may be in need of monitoring for the progression of the disease or condition. The patient may also be in on a treatment therapy that needs to be monitored for efficacy.

Peptide tracers have proven to be excellent imaging biomolecules. They can be readily labeled with gamma and positron emitting nuclides ($^{123}$I, $^{99m}$Tc and $^{18}$F, $^{124}$I, respectively), are rapidly cleared from healthy tissues, are relatively immunologically silent, and can be easily manufactured according to GMP standards for human use. Furthermore, peptides can be readily manipulated to increase stability in circulation and affinity for the target pathology (i.e., multimerization and cyclization).

The present invention is based in part on the finding that radio-iodinated protamine when injected into systemic AA mice was sequestered by amyloid deposits in the liver, kidney, pancreas, and spleen, as evidenced by microSPECT imaging. Protamine is a naturally occurring positively charged peptide that binds heparin. The present invention is also based in part on the finding that several peptides that are rich in positively charged amino acids, such as lysine and/or arginine, bind amyloids. As an example, the present invention shows that some of these peptides bind to formalin-fixed, paraffin-embedded, amyloid containing tissue sections from patients with AL κ and λ amyloidosis, Alzheimer's disease (Aβ), Transthyretin amyloidosis (ATTR), serum amyloid protein A amyloidosis (AA), fibrinogen a amyloidosis (AFibα), calcifying epithelium odontogenic tumor amyloid (AODAM), galectin 7 amyloidosis (AGal), Lect2 amyloidosis (ALECT2). The homologies exhibited by all amyloids are well established. For example, amyloids that are associated with a clinically heterogeneous group of diseases and can form from structurally distinct and functionally diverse precursor proteins, share a number of remarkably similar characteristics including fibril structure, fibril epitopes and accrual of similar accessory molecules including glycosaminoglycans (GAG) such as heparan sulfate proteoglycan (HSPG). These peptides have the potential of imaging all amyloids, irrespective of the precursor proteins that form the amyloids. Examples of some of the amyloids and their precursor proteins that the peptides may detect are shown in Table 1.

TABLE 1

Examples of Amyloids and Their Precursor Proteins

| Amyloid | Precursor Protein |
| --- | --- |
| ALλ | λ light chains |
| ALκ | κ light chains |
| Aβ | Amyloid β peptide in Alzheimer's disease |
| ATTR | Transthyretin |
| AA (human and canine) | Serum amyloid protein A |
| AFibα | Fibrinogen α |
| AGal | Galectin 7 |
| ACEOT | ODAM |
| ALECT2 | Lectin2 |

The present invention provides peptides that specifically bind amyloids. The peptides of the present invention may comprise or consist of from about 3 to about 55 amino acids. The peptides of the present invention may comprise or consist of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. The peptides of the present invention may have a molecular weight of between about 200 Da to about 6 kDa. The molecular weight of the peptides of the present invention may be about 300 Da, 400 Da, 500 Da, 1 Kda, 2 kDa, 3 kDa, 4 kDa, or 5 kDa.

The amino acids forming all or a part of the peptide of the present invention may be stereoisomers and modifications of naturally occurring amino acids, non-naturally occurring amino acids, post-translationally modified amino acids, enzymatically synthesized amino acids, derivatized amino acids, constructs or structures designed to mimic amino acids, and the like. The amino acids forming the peptides of the present invention may be one or more of the 20 common amino acids found in naturally occurring proteins (Table 2), or one or more of the modified and unusual amino acid. The amino acids may be a D- or L-amino acids.

TABLE 2

Amino Acids

| Amino Acid | 3-Letter | 1-Letter | Side chain polarity | Side chain charge (pH 7.4) |
|---|---|---|---|---|
| Alanine | Ala | A | nonpolar | Neutral |
| Arginine | Arg | R | polar | Positive |
| Asparagine | Asn | N | polar | Neutral |
| Aspartic acid | Asp | D | polar | Negative |
| Cysteine | Cys | C | nonpolar | neutral |
| Glutamic acid | Glu | E | polar | negative |
| Glutamine | Gln | Q | polar | neutral |
| Glycine | Gly | G | nonpolar | neutral |
| Histidine | His | H | polar | positive/neutral |
| Isoleucine | Ile | I | nonpolar | neutral |
| Leucine | Leu | L | nonpolar | neutral |
| Lysine | Lys | K | polar | positive |
| Methionine | Met | M | nonpolar | neutral |
| Phenylalanine | Phe | F | nonpolar | neutral |
| Proline | Pro | P | nonpolar | neutral |
| Serine | Ser | S | polar | neutral |
| Threonine | Thr | T | polar | neutral |
| Tryptophan | Trp | W | nonpolar | neutral |
| Tyrosine | Tyr | Y | polar | neutral |
| Valine | Val | V | nonpolar | neutral |

The peptides of the present invention may also comprise one or more modified amino acids. The modified amino acid may be a derivatized amino acid or a modified and unusual amino acid. Examples of modified and unusual amino acids include but are not limited to, 2-Aminoadipic acid (Aad), 3-Aminoadipic acid (Baad), β-Amino-propionic acid (Bala, β-alanine), 2-Aminobutyric acid (Abu, piperidinic acid), 4-Aminobutyric acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (AHyl), 3-Hydroxyproline (3Hyp), 4-Hydroxyproline (4Hyp), Isodesmosine (Ide), allo-Isoleucine (AIle), N-Methylglycine (MeGly, sarcosine), N-Methylisoleucine (MeIle), 6-N-Methyllysine (MeLys), N-Methylvaline (MeVal), Norvaline (Nva), Norleucine (Nle), and Ornithine (Orn).

Other examples of modified and unusual amino acids are described generally in Synthetic Peptides: A User's Guide, Second Edition, April 2002, Edited Gregory A. Grant, Oxford University Press; Hruby V J, Al-obeidi F and Kazmierski W: Biochem J 268:249-262, 1990; and Toniolo C: Int J Peptide Protein Res 35:287-300, 1990; the teachings of all of which are incorporated herein by reference.

The peptides of the present may comprise at least about 15% positively charged amino acids such as arginine and/or lysine. The peptides comprise from about 15% to about 50%, about 20% to about 45%, about 25% to about 40%, or about 30% to about 35% positively charged amino acids. In one embodiment, the peptides of the present invention may comprise the following amino acid sequence:

XBXXBXXXBXXBXXXBXXBXXXBXXBX,    (SEQ ID NO: 1)

wherein

X is any amino acid including a modified amino acid that is not charged; and,

B is a positively charged amino acid.

In one embodiment, the peptides of the present invention comprises SEQ ID NO: 1, wherein X is alanine, valine, serine, threonine, or glycine and B is arginine, lysine, or histidine. The peptides of the present invention may comprise or consist of SEQ ID NO: 1. The peptides of the present invention may have at most 55 amino acids and comprise the amino acid sequence as set forth in SEQ ID NO: 1.

In another embodiment, the peptide may comprise the following amino acid sequence:

BXZBXZXBZXBZXZBXZBXZXBZXBZ,    (SEQ ID NO: 2)

wherein,

B is arginine, lysine, or histidine;

X is isoleucine, leucine, methionine, valine, glycine, phenylalanine, tryptophan, tyrosine, serine, threonine, asparagine, or a modified amino acid that is not charged; and Z may be isoleucine, leucine, methionine, valine, glycine, phenylalanine, tryptophan, tyrosine, serine, threonine, asparagine, or a modified amino acid that is not charged.

The peptides of the present invention may comprise or consist of SEQ ID NO: 2. The peptides of the present invention may have at most 55 amino acids and comprise the amino acid sequence as set forth in SEQ ID NO: 2.

In certain embodiments, the peptides of the present invention may comprise or consist of the following amino acid sequence:

SRAQRAQARQARQAQRAQRAQARQARQ.    (SEQ ID NO: 3)

The peptides of the present invention may have at most 55 amino acids and comprise the amino acid sequence as set forth in SEQ ID NO: 3.

The peptides of the present invention may be a fusion protein comprising a second peptide as a leader sequence at the amino terminus, such as CGGY or GGGY for labeling with an agent for detection. Accordingly, the peptide of the present invention may have at most 55 amino acids and comprise an amino acid sequence as set forth in SEQ ID NO: 4.

CGGYSRAQRAQARQARQAQRAQRAQARQARQ.    (SEQ ID NO: 4)

The fusion protein may comprise other leader sequences such as a cell penetrating peptide (CPP) or a blood brain barrier (BBB) translocating peptide.

The present invention also provides other peptides and fusion proteins that are rich in positively charged amino acids for imaging amyloids. Some examples of such peptides are included in Table 3.

TABLE 3

Examples of Positively Charged Peptides and Fusion Proteins.

| Peptide Name | Amino Acid Sequence | # of Amino Acids | MW | pI | Net charge |
|---|---|---|---|---|---|
| p30 | CGGYSRPRARARARDQTR (SEQ ID NO: 5) | 18 | 2077.3 | 11.71 | 4 |
| p31 | CGGYSKAQKAQKAQKAQKAQKAQKAQKAQKAQ (SEQ ID NO: 6) | 31 | 3303.7 | 10.31 | 8 |
| p31R | CGGYSRAQRAQARQARQAQRAQRAQARQARQ (SEQ ID NO: 4) | 31 | 3527.9 | 12.22 | 8 |
| p32 | CGGYPRRRRSSSRPIRRRRPRRASRR (SEQ ID NO: 7) | 26 | 3252.7 | 12.52 | 13 |
| p33 | CGGYARKKAAKAARKKAAKAARKKAAKAVLVLVLVL (SEQ ID NO: 8) | 36 | 3722.6 | 11.29 | 12 |
| p34 | CGGYFAKLNCRLYRKANKSSK (SEQ ID NO: 9) | 21 | 2407.8 | 10.04 | 6 |
| p48 | CGGYSSSRPVRRRRRPRVSRRRRRGGRRRR (SEQ ID NO: 10) | 30 | 3752.3 | 12.64 | 16 |
| p49 | CGGYGDAKKKKDGKKAEPKNPRENKLKQPG (SEQ ID NO: 11) | 30 | 3270.7 | 9.85 | 6 |
| p50 | CGGYPKKGSKKAVTKAQKKDGKKR (SEQ ID NO: 12) | 24 | 2952.1 | 10.37 | 9 |
| p31-GGGY | GGGYSKAQKAQKAQKAQKAQKAQKAQKAQKAQ (SEQ ID NO: 13) | 31 | 3257.7 | 10.54 | 8 |
| p31 + 14 | CGGYSKAQKAQKAQKAQKAQKAQKAQKAQKAQKAQKAQKAQKAQKAQ (SEQ ID NO: 14) | 45 | 4812.5 | 10.53 | 12 |
| Syb3-p31 | RRLSYSRRRFCGGYSKAQKAQKAQKAQKAQKAQKAQKAQKAQ (SEQ ID NO: 15) | 41 | 4682.4 | 11.54 | 13 |
| TAT-p31 | YGRKKRRQRRRCGGYSKAQKAQKAQKAQKAQKAQKAQKAQKAQ (SEQ ID NO: 16) | 42 | 4845.6 | 11.76 | 16 |
| p31(1-24) | CGGYSKAQKAQKAQKAQKAQKAQKA (SEQ ID NO: 17) | 24 | 2520.9 | 10.14 | 6 |
| WAL14463 | TFFYGGSRGKRNNFKTEEYGGYSKAQKAQKAQKAQKAQKAQKAQKAQKAQ (SEQ ID NO: 18) | 49 | 5484.1 | 10.35 | 10 |
| WAL14465 | GGYSKAQKAQKAQKAQKAQKAQKAQKAQKAQGGTFFYGGSRGKRNNFKTEEY (SEQ ID NO: 19) | 51 | 5598.2 | 10.35 | 10 |
| p31GGGY + 14 | GGGYSKAQKAQKAQKAQKAQKAQKAQKAQKAQKAQKAQKAQKAQKAQ (SEQ ID NO: 20) | 45 | 4766.4 | 10.74 | 12 |
| p31R + 14 | CGGYSRAQRAQRAQRAQRAQRAQARQARQARQARQARQARQARQARQ (SEQ ID NO: 21) | 45 | 5148.7 | 12.48 | 12 |
| p31RGGGY | GGGYSRAQRAQARQARQAQRAQRAQARQARQ (SEQ ID NO: 22) | 31 | 3481.8 | 12.48 | 8 |

TABLE 3-continued

Examples of Positively Charged Peptides and Fusion Proteins.

| Peptide Name | Amino Acid Sequence | # of Amino Acids | MW | pI | Net charge |
|---|---|---|---|---|---|
| p31RG GGY + 14 | GGGYSRAQRAQARQARQAQRAQR AQARQARQAQRAQRAQARQARA (SEQ ID NO: 32) | 45 | | | |

In certain embodiments, the amino acid sequence of the peptides of the present invention are sequential, without any modified and unusual amino acids interrupting the sequence of D- or L-amino acids. In other embodiments, the sequence may comprise one or more modified and unusual amino acids. In particular embodiments, the sequence of the peptides may be interrupted by one or more modified and unusual amino acids. Accordingly, the present invention also provides pseudopeptides and peptidomimetics, including structures which have a non-peptidic backbone that specifically binds amyloids.

The present invention also provides dimers or multimers of peptides that have enhanced affinity for amyloids as compared to its monomers.

The peptides of the present invention may be made by any technique known to those of skill in the art, including chemical synthesis, recombinant means using standard molecular biological techniques, or the isolation of peptides from natural sources. The peptides may be synthesized in solution or on a solid support in accordance with conventional techniques. Various automatic synthesizers are commercially available and can be used in accordance with known protocols. (See, for example, Stewart and Young, Solid Phase Peptide Synthesis, 2d ed. Pierce Chemical Co., 1984; Tam et al., J. Am. Chem. Soc., 105:6442, 1983; Merrifield, Science, 232: 341-347, 1986; and Barany and Merrifield, The Peptides, Gross and Meienhofer, eds., Academic Press, New York, pp. 1-284, 1979, each is incorporated herein by reference in its entirety.)

Alternatively, recombinant DNA technology may be employed wherein a nucleotide sequence which encodes a peptide of the invention is inserted into an expression vector, transformed or transfected into an appropriate host cell, cultivated under conditions suitable for expression, and isolating the peptide.

In certain embodiments, the peptides of the present invention may be a naturally occurring peptide and may be obtained by isolation or purification from its naturally sources. Protein purification techniques involve, at one level, the homogenization and crude fractionation of the cells, tissue or organ to peptide and non-peptide fractions. Other protein purification techniques include, for example, precipitation with ammonium sulfate, polyethylene glycol (PEG), antibodies and the like, or by heat denaturation, followed by: centrifugation; chromatography steps such as ion exchange, gel filtration, reverse phase, hydroxylapatite and affinity chromatography; isoelectric focusing; gel electrophoresis, for example polyacrylamide gel electrophoresis; and combinations of these and other techniques Various chromtographic techniques include but are not limited to ion-exchange chromatography, gel exclusion chromatography, affinity chromatography, immunoaffinity chromatography, and reverse phase chromatography. A particularly efficient method of purifying peptides is fast performance liquid chromatography (FPLC) or even high performance liquid chromatography (HPLC).

The order of conducting the various purification steps may be changed, or that certain steps may be omitted, and still result in a suitable method for the preparation of a substantially purified peptide.

The peptides of the present invention may be a part of a polypeptide or protein and may be produced by biochemical or enzymatic fragmentation of the polypeptide or protein. Accordingly, the peptides of the present invention may be (a) naturally-occurring, (b) produced by chemical synthesis, (c) produced by recombinant DNA technology, (d) produced by biochemical or enzymatic fragmentation of larger molecules, (e) produced by methods resulting from a combination of methods a through d listed above, or (f) produced by any other means for producing peptides.

During chemical synthesis, the peptides may be modified at its N- or C-terminus, thereby providing for improved stability and formulation, resistance to protease degradation, and the like. Examples of modifications of amino acids include pegylation, acetylation, alkylation, formylation, amidation. Moreover, various amino acids which do not naturally occur along the chain may be introduced to improve the stability of the peptides.

The present invention also provides fusion peptides comprising the peptides of the present invention fused to a second peptide or polypeptide. The second peptide or polypeptide may be linked at the N- or C-terminus of the peptide of the present invention. In one embodiment the second peptide of the fusion peptide may be a short flanking peptide, such as but not limited to one to five amino acids in length. The one to five amino acids may be selected from the group consisting of alanine, isoleucine, leucine, methionine, valine, glycine, phenylalanine, tryptophan, tyrosine, serine, threonine, asparagine, glutamine, cysteine, proline, aspartic acid, glutamic acid, arginine, histidine, lysine, other amino acids, and a combination thereof. The one to five amino acids may be a leader sequence linked at the amino terminus of the peptide.

In one embodiment, an aromatic amino acid, such as tyrosine, is included as one of five amino acids of the flanking peptide. Tyrosine is useful for labeling the peptides of the present invention with iodine isotopes. An aromatic amino acid, such as tyrosine, is also useful for measuring peptide concentration using absorbance at 280 nm ($A_{280}$). In another embodiment, a cysteine is included as one of the five amino acids of the flanking peptide. Cysteine is useful for directly incorporating radionuclides such as 99m-technetium or indirectly through radionuclide chelators as linking reagents, which spares the ε-amino group on lysine, the critically important positively charged amino acid, within the peptide from being used in covalent attachments. Cysteine is also useful for facilitating the labeling of peptides of the present invention with radioisotopes. As an example, the flanking peptide may be CGG or CGGG which is useful for labeling the peptides of the present invention with $^{99m}$Tc. The flanking peptide may also have the sequence CGGY, and the fusion peptide of the present invention may have the following amino acid sequence:

CGGYSKAQKAQAKQAKQAQKAQKAQKAQAKQAKQ (SEQ ID NO: 6)

Cysteine is also useful for facilitating the labeling of peptides of the present invention with biotin, fluorophores, or other ligands via conjugation. Moreover, a cysteine on the leader peptide allows the generation of covalently bound dimer molecules that might increase the relative affinity of the peptides for their targets.

The second peptide in the fusion peptide may also be a peptide that selectively targets the peptide of the present invention to a specific site, and the second peptide may also be fused to the peptide of the present invention at the N- or C-terminus. For example, the second peptide may be a cell penetrating peptide (CPP) or blood brain barrier (BBB) translocating peptide, which enhances the penetration of molecules across the BBB. Examples of CPPs include but are not limited to model amphipathic peptide, pAntp$_{43-68}$, transportan, SBP, FBP, Tat$_{48-60}$, SynB1, and SynB2 (see Table 4).

TABLE 4

Cell Penetrating Peptides

| Peptide | Sequence |
|---|---|
| Model amphipathic peptide | KLALKLALKALKAALKLA (SEQ ID NO: 23) |
| pAntp$_{43-68}$ | RQIKIWFQNRRMKWKK SEQ ID NO: 24) |
| Transportan | GWTLNSAGYLLGKINLKALAALAKKIL (SEQ ID NO: 25) |
| SBP | MGLGLHLLVLAAALQGAWSQPKKKRKV (SEQ ID NO: 26) |
| FBP | GALFLGWLGAAGSTMGAWSQPKKKRKV (SEQ ID NO: 27) |
| Tat$_{48-60}$ | GRKKRRQRRRPPQ (SEQ ID NO: 28) |
| SynB1 | RGGRLSYSRRRFSTSTGR (SEQ ID NO: 29) |
| SynB3 | RRLSYSRRF (SEQ ID NO: 30) |
| Angiopep | TFFYGGSRGKRNNFKTEEY (SEQ ID NO: 31) |

The second peptide in the fusion peptide of the present invention also may be a leader sequence from other species to permit the recombinant expression of a protein in a heterologous host. Another useful fusion includes the addition of an immunologically active domain, such as an antibody epitope, to facilitate purification of the fusion peptide. Moreover, inclusion of a cleavage site at or near the fusion junction will facilitate removal of the extraneous polypeptide after purification.

Methods of generating fusion peptides are well known to those of skill in the art. Such proteins can be produced, for example, by chemical attachment using bifunctional cross-linking reagents, by de novo synthesis of the complete fusion peptide, or by attachment of a DNA sequence encoding the targeting peptide to a DNA sequence encoding the second peptide or protein, followed by expression of the intact peptide or fusion peptide.

The present application also provides isolated nucleic acids encoding the peptides and fusion peptides of the present invention. The isolated nucleic acid may be incorporated into a eukaryotic or a prokaryotic expression vector. The vector may be a plasmid, a cosmid, a yeast artificial chromosome (YAC), a bacterial artificial chromosome (BAC), a virus or a bacteriophage. The isolated nucleic acid may be operatively linked to a leader sequence or other sequences that assist in the isolation and purification of the peptide.

The nucleic acid encoding the peptides and fusion peptides of the present invention includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded peptide or fusion peptide. The nucleic acid may be derived from genomic DNA, complementary DNA (cDNA) or synthetic DNA. The nucleic acid may also comprise a natural intron or an intron derived from another gene for incorporation into an expression vector.

It is contemplated that the peptides and fusion peptides of the present invention may be encoded by any nucleic acid sequence that encodes the appropriate amino acid sequence. The nucleic acid encoding a desired amino acid sequence may be designed using standardized codon tables. The codons selected for encoding each amino acid may be modified to optimize expression of the nucleic acid in the host cell of interest. Codon preferences for various species of host cell are well known in the art.

Nucleic acids encoding the peptides and fusion peptides of the present invention may be produced by chemical synthesis, purchased from commercial sources, standard gene cloning methods, or any other method. The nucleic acids may be inserted in a vector for expression of the encoded peptide or fusion peptide. The nucleic acids encoding the peptides and fusion peptides of the present invention or the vector comprising the nucleic acids may be introduced into a host cell by transfection or transformation under conditions that would allow expression of the encoded peptides and fusion peptides. Subsequently, the expressed peptides and fusion peptides may be isolated and/or purified and used.

Expression vectors may be employed to express the peptide or fusion peptide of the present invention. A number of nucleic acid vectors, such as expression vectors are commercially available. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells may be included in the vectors.

The terms "expression construct" or "expression vector" are meant to include any type of genetic construct containing a nucleic acid encoding the peptide or fusion peptide of the present invention, in which part or all of the nucleic acid coding sequence is capable of being transcribed. The nucleic acid encoding the peptide or fusion peptide of the present invention may be under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The particular promoter used to control the expression of a nucleic acid encoding the peptide or fusion peptide of the present invention directs the expression of the nucleic acid in a host cell. Examples of promoters include but are not limited to the human cytomegalovirus (CMV) immediate early gene promoter, the SV40 early promoter, the Rouse sarcoma virus long terminal repeat, rat insulin promoter, and glyceraldehyde-3-phosphate dehydrogenase promoter can be used to obtain high-level expression of the coding sequence of interest. The use of other viral or mammalian cellular or bacterial phage promoters that are known in the art to achieve expression of a coding sequence of interest is contemplated as well, provided that the sufficient levels of expression is achieved for producing the peptide and/or fusion peptide of the present invention.

The vector may comprise a polyadenylation signal to effect proper polyadenylation of the gene transcript, such as a human growth hormone and SV40 polyadenylation signals. Also contemplated as an element of the expression construct is a terminator. These elements can serve to enhance message levels and to minimize read through from the construct into other sequences.

Host cells for expressing the peptides and fusion peptides of the present invention includes prokaryotes or eukaryotes. Suitable prokaryote hosts include bacterial host cells such as E. coli. Various strains of E. coli include but are not limited to HB101, DH5, DH10, and MC1061. Suitable eukaryote hosts include yeasts and mammalian cells. Examples include but are not limited to Saccharomyces (e.g. S. cerevisiae); 293 (human embryonic kidney) (ATCC CRL-1573); 293F (Invitrogen, Carlsbad Calif.); 293T and variant 293T/17 (293tsA1609neo and variant ATCC CRL-11268) (human embryonic kidney transformed by SV40 T antigen); COS-1 and COS-7 (monkey kidney CVI line transformed by SV40) (ATCC CRL1651); BHK (baby hamster kidney cells) (ATCC CRL10); CHO (Chinese hamster ovary cells); mouse Sertoli cells; CVI (monkey kidney cells) (ATCC CCL70); VERO76 (African green monkey kidney cells) (ATCC CRL1587); HeLa (human cervical carcinoma cells) (ATCC CCL2); MDCK (canine kidney cells) (ATCC CCL34); BRL3A (buffalo rat liver cells) (ATCC CRL1442); W138 (human lung cells) (ATCC CCL75); HepG2 (human liver cells) (HB8065); and MMT 060652 (mouse mammary tumor) (ATCC CCL51).

Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

The peptides and fusion peptides of the present invention may be produced by transforming or transfecting host cells with nucleic acids encoding the peptides and fusion peptides. Methods for transforming and transfecting host cells with nucleic acids are well-known and routinely performed. The nucleic acid sequences encoding the peptides and fusion peptides of the present invention also may be introduced into cultured mammalian cells by, for example, calcium phosphate-mediated transfection (Wigler et al., Cell 14: 725, 1978; Corsaro and Pearson, Somatic Cell Genetics 7: 603, 1981; Graham and Van der Eb, Virology 52: 456, 1973.) Other techniques for introducing cloned DNA sequences into mammalian cells, such as electroporation (Neumann et al., EMBO J. 1: 841-845, 1982), or lipofection may also be used. In order to identify cells that have integrated the cloned DNA, a selectable marker is generally introduced into the cells along with the gene or cDNA of interest. Examples of selectable markers for use in cultured mammalian cells include genes that confer resistance to drugs, such as neomycin, hygromycin, and methotrexate. The selectable marker may be an amplifiable selectable marker, for example, the DHFR gene and the $DHFR^r$. Selectable markers are reviewed by Thilly (Mammalian Cell Technology, Butterworth Publishers, Stoneham, Mass.) and the choice of selectable markers is well within the level of ordinary skill in the art.

The present invention provides compositions comprising one or more peptides and/or one or more fusion peptides of the present invention. The compositions may further comprise a carrier. The present invention also provides pharmaceutical compositions comprising one or more peptides and/ or fusion peptides of the present invention. Such pharmaceutical compositions comprise an effective amount of the peptide or fusion peptide for binding to and detection of amyloids and a pharmaceutically acceptable carrier.

Pharmaceutically acceptable carriers include solid or liquid carriers or components which may be added to enhance or stabilize the composition, or to facilitate preparation of the composition include, without limitation, syrup, water, isotonic saline solution, 5% dextrose in water or buffered sodium or ammonium acetate solution, oils, glycerin, alcohols, among others. Examples of oils include those of petroleum, animal, vegetable or synthetic origin, such as peanut oil, soybean oil, mineral oil, and sesame oil. The carrier may also include a sustained release material such as glyceryl monostearate or glyceryl distearate, alone or with a wax. Other suitable pharmaceutical carriers include but are not limited to include starch, glucose, lactose, sucrose, gelatin, malt, rice, flour, chalk, silica gel, sodium stearate, glycerol monostearate, talc, sodium chloride, dried skim milk, propylene, glycol, water, ethanol, flavoring agents, preservatives, coloring agents diluents, granulating agents, lubricants, binders, and the like.

Water may be the preferred carrier when the pharmaceutical composition is administered intravenously. Saline solutions and aqueous dextrose and glycerol solutions can also be employed as liquid carriers, particularly for injectable solutions. The composition, if desired, can also contain minor amounts of wetting or emulsifying agents, or pH buffering agents. Such compositions can take the form of solutions, suspensions, emulsion, tablets, pills, capsules, powders, sustained-release formulations and the like. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of other suitable pharmaceutical carriers are described in "Remington's Pharmaceutical Sciences" by E. W. Martin.

The overall formulation should suit the mode of administration. The compositions according to the present invention may be formulated in accordance with routine procedures adapted, for example, to the intravenous administration to a subject. The subject may be a mammal, such as a human being. Administration of the compositions according to the present invention may be via any common route so long as the target tissue is available via that route. This includes oral, nasal, buccal, rectal, vaginal or topical. Alternatively, administration may be by intradermal, subcutaneous, intramuscular, intraperitoneal, intraarterial or intravenous injection.

Compositions for intravenous administration are solutions in sterile isotonic aqueous buffer. The compositions may also include a solubilizing agent and a local anesthetic such as lignocaine to ease pain at the site of the injection. The ingredients are supplied either separately or mixed together in unit dosage form, for example, as a dry lyophilized powder or water free concentrate in a hermetically sealed container such as an ampule indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

The peptides and fusion peptides of the present invention are useful for specific binding to or selective targeting of amyloids. As used herein, the terms "selective binding" and "selective targeting" are used interchangeably in reference to amyloids. Accordingly, the peptides can be used to detect amyloids. The compositions and pharmaceutical compositions comprising the peptides and fusion peptides of the present invention are administered to a subject for detecting the presence or absence of amyloids in the subject.

In certain embodiments, the peptides and fusion peptides of the present invention may be attached to imaging agents useful for imaging of amyloids in organs and tissues. For example, a peptide of the present invention may be attached to an imaging agent, provided to a subject and the precise location of the amyloid may be determined by standard imaging techniques. Peptides that are non-selective for amyloids may be used as control for comparison. Thus, the biodistribution of the targeting peptides of the present invention may be compared to the biodistribution of one or more non-selective or control peptides to provide even greater discrimination for detection and/or localization of amyloids.

Methods for imaging amyloids include but are not limited to magnetic resonance imaging (MRI), computed axial tomography (CAT) scanning, positron emission tomography (PET), ultrasonic imaging, x-rays, radionuclide imaging, single photon emission computed tomography (SPECT), and multiphoton microscopy.

To increase the sensitivity of scans, various contrast media may be used. The contrast media for scans may include all molecules that attenuate x-rays. For positron emission tomography and radionuclide imaging, radioisotopes may be used. All positron emitting isotopes are useful for positron emission tomography radionuclide imaging, and all γ-photon emitting isotopes are useful for radionuclide imaging.

Contrast agents for ultrasonic imaging include positive agents and negative agents. Positive agents reflect the ultrasonic energy and thus they produce a positive (light) image. Correspondingly, negative agents enhance transmissibility or sonolucency and thus produce a negative (dark) image. A variety of substances—gases, liquids, solids, and combinations of these—has been investigated as potential contrast-enhancing agents. Examples of solid particle contrast agents disclosed in U.S. Pat. No. 5,558,854 include but not limited to IDE particles and SHU454. European Patent Application 0231091 discloses emulsions of oil in water containing highly fluorinated organic compounds for providing enhanced contrast in an ultrasound image. Emulsions containing perfluorooctyl bromide (PFOB) have also been examined as ultrasound imaging agents. U.S. Pat. No. 4,900,540 describes the use of phospholipid-based liposomes containing a gas or gas precursor as a contrast-enhancing agent.

Imaging agents may be attached to peptides and fusion peptides of the present invention using known methods. Certain attachment methods involve the use of a metal chelate complex employing, for example, an organic chelating agent such a DTPA. Acceptable chelates are known in the field. They include but are not limited to 1,4,7,10-tetraazacyclododecane-N,N',N",N'"-tetraacetic acid (DOTA); 1,4,7,10-tetraazacyclododecane-N,N',N"-triacetic acid (DO3A); 1,4,7-tris(carboxymethyl)-10-(2-hydroxypropyl)-1,4,7,10-tetraazacyclododecane (HP-DO3A); diethylenetriaminepentaacetic acid (DPTA); and many others.

Several classes of compounds have potential as MRI contrast agents. These classes include supraparamagnetic iron oxide particles, nitroxides, and paramagnetic metal chelates (Mann et al., 1995). A strong paramagnetic metal is preferred. Normally, paramagnetic lanthanides and transition metal ions are toxic in vivo. Thus, it is necessary to incorporate these compounds into chelates with organic ligands. The peptides and fusion peptides of the present invention may be used to enhance the targeting of such chelated metals to amyloids, which allows for the reduction in the total dose of imaging composition otherwise required.

Paramagnetic metals of a wide range are suitable for chelation. Suitable metals include those having atomic numbers of 22-29 (inclusive), 42, 44 and 58-70 (inclusive), and having oxidation states of 2 or 3. Examples of such metals include but are not limited to chromium (III), manganese (II), iron (II), cobalt (II), nickel (II), copper (II), praseodymium (III), neodymium (III), samarium (III), gadolinium (III), terbium (III), dysprosium (III), holmium (III), erbium (III), ytterbium (III), and vanadium (II). Ions useful in other contexts, such as X-ray imaging, include but are not limited to lanthanum (III), gold (III), lead (II), and especially bismuth (III).

Among the radioisotopes that can be used to label peptides and fusion peptides of the present invention that are suitable for localization studies are gamma-emitters, positron-emitters, X-ray-emitters and fluorescence-emitters. Appropriate radioisotopes for labeling peptides and fusion proteins include astatine$^{211}$, bromine$^{76}$, $^{14}$-carbon, $^{11}$carbon, $^{51}$chromium, $^{36}$chlorine, $^{57}$cobalt, $^{58}$cobalt, copper$^{67}$, copper$^{64}$, $^{152}$europium, fluorine$^{18}$, gallium$^{67}$, Gallium$^{68}$, $^{3}$hydrogen, iodine$^{123}$, iodine$^{124}$, iodine$^{125}$, iodine$^{126}$, iodine$^{131}$, indium$^{111}$, indium$^{113m}$, $^{59}$iron, $^{177}$lutetium, mercury$^{107}$, mercury$^{203}$, $^{32}$phosphorus, rhenium$^{186}$, rhenium$^{188}$, ruthenium$^{95}$, ruthenium$^{97}$, ruthenium$^{103}$, ruthenium$^{105}$, rhenium$^{99m}$, rhenium$^{105}$, rhenium$^{101}$, $^{75}$selenium, $^{35}$sulphur, technitium$^{99m}$, tellurium$^{121m}$tellurium$^{122m}$, tellurium$^{125m}$, thulium$^{165}$, thulium$^{167}$, thulium$^{168}$, and yttrium$^{90}$. The halogens may be used more or less interchangeably as labels. The gamma-emitters, iodine$^{123}$ and technetium$^{99m}$, may also be used because such radiometals are detectable with a gamma camera and have favorable half lives for imaging in vivo. The positron-emitters $^{18}$-fluorine or $^{124}$iodine which are suitable for PET imaging and have suitable half lives for peptide imaging may also be used. Peptides and fusion peptides of the present invention may be labeled with indium$^{111}$ or technetium$^{99m}$ via a conjugated metal chelator, such as DTPA (diethlenetriaminepentaacetic acid) or covalently and directly to the flanking peptide that contains a Cys residue.

Radioactively labeled peptides or fusion peptides of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Peptides or fusion peptides according to the invention may be labeled with technetium$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent, such as SnCl$_2$, a buffer solution such as sodium-potassium phthalate solution, and the peptide. Intermediary functional groups that are often used to bind radioisotopes that exist as metallic ions to peptides are diethylenetriaminepenta-acetic acid (DTPA) and ethylene diaminetetra-acetic acid (EDTA), as mentioned earlier.

Other useful labels include fluorescent labels, chromogenic labels, and biotin labels. Fluorescent labels, include but are not limited to rhodamine, fluorescein isothiocyanate, fluorescein sodium, renographin, and Texas Red sulfonyl chloride. In certain embodiments, the peptides and fusion peptides of the present invention may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Peptides and fusion peptides of the present invention also may be reacted with an enzyme in the presence of a coupling agent such as glutaraldehyde or periodate. Conjugates with fluorescein markers are prepared in the presence of these coupling agents or by reaction with an isothiocyanate.

The peptides and fusion peptides of the present invention serve as agents that target and bind amyloids to enable detection of amyloids. The peptides and fusion peptides of the present invention can be used to determine whether a subject has amyloid and whether a subject is suffering from amyloidosis or amyloid mediated condition.

The present invention provides a method for detecting amyloids in a subject. The method comprises administering a pharmaceutical composition comprising an effective amount of one or more peptides or fusion peptides of the present invention to a subject and detecting the peptides or fusion peptides bound to the amyloids. The peptides may be labeled with an imaging agent, such as a radioisotope. The peptide has specific binding affinity for the deposits and the binding is detectable. The binding of the peptides or fusion peptides to the amyloids may be detected by MRI, CAT scan, PET imaging, ultrasound imaging, SPECT imaging, X-ray imaging, fluorescence imaging, or radionuclide imaging.

In one embodiment, the invention provides a method for targeting amyloid in the body of an individual suffering from a bodily disorder associated with amyloidosis. According to this embodiment of the invention, a peptide that specifically binds to amyloids is systemically introduced into the body of an individual. The peptide binds amyloids within the body of the individual. The targeting of amyloids may be used for diagnostic purposes. For example, the peptide may be, or may contain or be attached to, a label or marker that is detectable. In this way, upon creating an image of the body or of a body part, an image of the deposition pattern of the peptide, and thus of the amyloid, in the body or body part may be obtained.

Accordingly, in one embodiment, the present invention provides a method of diagnosing amyloid mediated condition or disease comprising administering to a subject a pharmaceutical composition comprising one or more peptides or fusion peptides of the present invention, wherein the peptides or fusion peptides have been labeled with an imaging agent and imaging the peptides or fusion peptides in the subject to detect the presence of amyloids, thereby diagnosing an amyloid mediated condition in the subject.

In another embodiment, the present invention provides a method of monitoring the progression of amyloid mediated condition comprising administering to a subject diagnosed with an amyloid mediated condition, a pharmaceutical composition comprising one or more peptides or fusion peptides of the present invention, wherein the peptides or fusion peptides have been labeled with an agent and detecting the peptides or fusion peptides in the subject to monitor the presence of amyloids in the presence. The detection of the peptides or fusion peptides in the subject may be performed by imaging or other known methods.

The methods of the present invention, including detecting the presence of amyloids, and diagnosing or monitoring an amyloid mediated condition, may further comprise quantitating the amount of amyloids in the subject. Quantitation may be achieved using standard methods such as drawing regions of interest around patient organs or tissues seen in the radionuclide image and thereby determining the amount of radioactivity within that region. This method of quantifying the distribution of radiolabeled tracer molecules in patients is particularly accurate when PET images are used. The methods of the present invention may also further comprise comparing the image of amyloids in a subject to an image of a control subject. Examples of a control subject may be a subject that is not diagnosed with amyloid mediated condition or a subject administered with a control peptide. When the method is for monitoring the progression of amyloid mediated condition, the method may further comprise comparing the recently obtained image to an image obtained earlier in time to determine whether there is an increase or decrease in the amount of amyloids, thereby monitoring the progression of the amyloid mediated condition in the subject. Alternatively, the image may be obtained after treatment or therapy, and the image may be compared to an image obtained prior to treatment or therapy. Accordingly, the image could be used to monitor the response of the subject to treatment or therapy.

In one embodiment, methods of the present invention including detecting the presence of amyloids and diagnosing or monitoring an amyloid mediated condition in a subject comprises administering a peptide or fusion peptide comprising an amino acid sequence as set forth in SEQ ID NO: 32, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or SEQ ID NO: 22 and may consist of at most 55 amino acids. In another embodiment, the peptide or fusion peptide may be peptides p31, p31R, p32, or p48.

The amount of the diagnostic and imaging peptides or fusion peptides of the present invention which will be effective in the diagnosis, monitoring, or imaging of an amyloid mediated condition can be determined by standard clinical techniques. In addition, in vivo and/or in vitro assays may optionally be employed to help identify optimal dosage ranges. The precise dose to be employed in any particular formulation will also depend on the route of administration, and the seriousness of the disease or disorder, and should be decided according to the judgment of the practitioner and each patient's circumstances.

The pharmaceutical compositions comprising the labeled peptides or fusion peptides of the present invention for the imaging of amyloids may be administered by the parenteral route, e.g., intravenously, intraperitoneally, subcutaneously, intradermally, or intramuscularly. In addition, it may be desirable to introduce the pharmaceutical compositions of the invention into the central nervous system by any suitable route, including intraventricular and intrathecal injection.

The peptides and fusion peptides of the present invention may also be used to detect and quantitate amyloids by in vitro methods. The peptides or fusion peptides of the present invention may be used to detect amyloids in a tissue sample obtained from a subject for diagnosis or treatment of the subject and for monitoring the progression of a subject's condition or the response of the subject to therapy. For example, biotinylated peptides or fusion peptides can be used to visualize using standard immunohistochemical techniques the distribution of amyloid within a fresh-frozen or formalin-fixed paraffin-embedded tissue section that has been prepared from patient tissues. The presence of amyloid-bound peptide or fusion peptide can be discerned using any of a number of methods including the use of streptavidin-conjugated horseradish peroxidase followed by addition of a peroxidase substrate such as diaminobenzidene. The peptides or fusion peptides of the present invention may also be used to bind amyloids in an amyloid extract or to bind synthetic amyloid fibrils. Surface plasmon resonance and ELISA may be employed for detecting such binding.

In one embodiment, to enhance the uptake of the labeled peptides through the blood brain barrier (BBB), the peptides of the present invention may be fused to a CPP, as described earlier. In another embodiment the labeled peptides and fusion peptides of the present invention may be modified to enhance uptake, delivery, or permeability across cells, such as endothelial cells. As an example, the peptides and fusion peptides may be modified with naturally occurring or synthetic polyamines, such as putresceine, spermidine, spermine, or thermine (see U.S. Pat. No. 7,371,365, incorporated by reference in its entirety) to enhance its permeability across the BBB into the central nervous system for imaging amyloids in the brain, for example amyloid plaques of an Alzheimer patients.

The peptides and fusion peptides of the present invention may be modified by chemical conjugation to enhance permeability across cells, to enhance stability, or for detection of amyloids.

There are numerous cross-linking agents available for conjugating the peptides or fusion peptides to another molecule. However, the resulting conjugated peptide or fusion peptide must retain its ability to bind amyloids. Accordingly, the functional groups on the peptide or fusion peptide that are available for conjugation are not involved for binding to amyloids. For example, the positively charged amino acids on the peptide are critical for binding amyloids. Thus, the functional groups involved in the cross-linking reaction should not involve the functional groups on positively charged amino acids, such as lysine, arginine, and histidine. Examples of some cross-linking approaches are discussed below.

Imido esters are the most specific acylating reagents for reaction with amine groups whereby in mild alkaline pH, imido esters react only with primary amines to form imidoamides. The product carries a positive charge at physiological pH, as does the primary amine it replaces and therefore, does not affect the overall charge of the protein. As an example, maleimide is useful for incorporating radionuclide on cysteine for forming biotinylated peptides using the cysteine residue.

Homobifunctional N-hydroxysuccinimidyl ester conjugation is also a useful cross-link approach to crosslink amine-containing proteins. Homobifunctional sulfhydryl reactive cross-linkers include bismaleimidhexane (BMH), 1,5-difluoro-2,4-dinitrobenzene (DFDNB), and 1,4-di-(3',2'-pyridyldithio) propionamido butane (DPDPB).

Many heterobifunctional cross-linkers are commercially available with the majority containing an amine-reactive functional group on one end and a sulfhydryl-reactive group on the other end. Multiple heterobifunctional haloacetyl cross-linkers are available, as are pyridyl disulfide cross-linkers. Carbodiimides are a classic example of heterobifunctional cross-linking reagents for coupling carboxyls to amines resulting in an amide bond.

The present invention also provides a kit comprising one or more peptides or fusion peptides of the present invention. The kits may include a suitable container means for containing one or more peptides or fusion peptides. The kits may also include a control peptide or control fusion peptide, a labeling agent, means for delivering the peptide or fusion peptide to a sample or subject, and/or a means for detecting the binding of the peptide or fusion peptide to amyloids The container means of the kits will generally include at least one vial, test tube, flask, bottle, syringe or other container means, into which the peptides or fusion proteins may be placed, and suitably aliquoted. Where the kit contains an additional component, the kit will also generally contain additional containers into which the component may be placed.

Means for delivering the peptide or fusion peptide to amyloids may include syringes, droppers, pipettes, and other applicators.

Means for detecting the binding of the peptide or fusion peptide to amyloids may include reagents for performing a histochemical or fluorescence assay on a tissue sample or for imaging a subject. The kit may be a tissue staining kit containing the various reagents for tissue samples. The kit may be an imaging kit containing various reagents for imaging a subject or a tissue.

The subject may be a patient in need of treatment, diagnosis, or monitoring of an amyloid mediated disease or condition. The subject may also be a patient in need of monitoring the efficacy of a treatment protocol, therapy, or a drug associated with treating the amyloid mediated disease or condition. The subject may be a patient suspected of having an amyloid mediated disease or condition.

The amyloid mediated condition includes but are not limited to Creutzfeld-Jakob Disease (CJD), Kuru, transmissible cerebral amyloidosis, transmissible virus dementias, familial CJD, scrapie, transmissible mink encephalopathy, bovine spongiform encephalopathy (BSE), inflammation-associated amyloid, type II diabetes, primary amyloidosis, feline spongiform encephalopathy, non-transmissible cerebral amyloidosis, prion-mediated diseases, dialysis-related amyloidosis, light chain-related amyloidosis, cerebral amyloid angiopathy, and Alzheimer's disease.

Without further description, it is believed that one of ordinary skill in the art can, using the preceding description and the following illustrative examples, make and utilize the claimed invention. The following working examples therefore, specifically point out preferred embodiments of the present invention, and are not to be construed as limiting in any way the remainder of the disclosure. All articles, publications, patents and documents referred to throughout this application are hereby incorporated by reference in their entirety.

EXAMPLES

Example 1

$^{125}$I-Labeled, Heparin-Reactive Protamine as a Novel Amyloid Imaging Reagent Amyloid deposits contain, in addition to protein fibrils, a significant concentration of heparan sulfate proteoglycans (HSPG). Data suggest that the chemical structure of amyloid-associated heparan sulfate differs from that found ubiquitously in the ECM of essentially all normal tissues. Based upon these observations and the findings that certain HS-reactive scFv selectively bind amyloid deposits in AA mice and did not accumulate significantly in healthy tissues, the deposition of heparin-binding protamine in a transgenic mouse model of AA was investigated.

A heparin-binding peptide derived from protamine was synthesized, purified by reverse phase HPLC. Following radioiodination, $^{125}$I-labeled protamine ($^{125}$I-protamine) was administered to animals with severe systemic AA amyloidosis mice or to amyloid-free mice and allowed to circulate for 1 hour, 2 hours, 4 hours, 8 hours or 24 hours. At each time point high-resolution microSPECT/CT images were acquired and the tissue distribution of the radioactivity determined by gamma counting. Finally, 6 μm-thick tissue sections were prepared for autoradiography and histological evaluation of the micro-distribution of the radiolabeled peptides and amyloid deposits, respectively.

In control mice the $^{125}$I-protamine was rapidly dehalogenated and the liberated $^{125}$I sequestered by the stomach which was visible together with the thyroid in SPECT images up to 8 h pi. In contrast, $^{125}$I-protamine when injected into AA mice was sequestered by amyloid deposits in the liver, kidney, pancreas and spleen with smaller amounts in the stomach, as evidenced by microSPECT imaging. The calculated tissue:muscle ratios for these organs (all sites of AA deposition) was at least 2-fold greater in mice with AA, indicating specific retention of the protamine peptide by amyloid. Micro-autoradiography confirmed that $^{125}$I-protamine preferentially associated with the AA amyloid in these and other organs and tissues, notably within the liver. In amyloid-free mice there was little or no specific accumulation of $^{125}$I-protamine in any organ or tissue. These data indicate that even though HS is expressed in normal tissue, the heparin-reactive peptide protamine offers a novel, potentially pan-amyloid, binding reagent that, when radiolabeled, could be used to diagnose disease and monitor response to therapy using molecular imaging techniques.

Example 2

In Vivo and In Vitro Evaluation of Positively Charged Peptides as Amyloid Imaging Agents Peptide tracers have proven to be excellent imaging biomolecules—they can be readily labeled with gamma and positron emitting nuclides ($^{123}$I, $^{99m}$Tc and $^{18}$F, $^{124}$I, respectively), are rapidly cleared from healthy tissues, are relatively immunologically silent, and can be easily manufactured according to GMP standards for human use. Furthermore, peptides can be readily manipulated to increase stability in circulation and affinity for the target pathology (i.e., multimerization and cyclization).

Based on the data obtained with protamines, in the Examples below, peptides that are positively charged are selected. They were labeled with radioiodine (I-125 and I-123) or technetium (Tc-99m) tested for in vivo binding to systemic AA amyloid deposits in the transgenic rapidly inducible amyloid disease (TRIAD) murine model by microSPECT or microPET imaging. The tissue biodistribution of each were assessed by gamma counting and the micro-distribution determined by autoradiography. Further, preliminary examinations were performed of the binding of biotinylated forms of these peptides with formalin-fixed, paraffin-embedded, amyloid-containing tissue sections from patients with AL κ and λ amyloidosis, Alzheimer's disease, Transthyretin amyloidsis (ATTR), serum amyloid protein A amyloidosis (AA), fibrinogen α amyloidosis (AFibα), calcifying epithelium odontogenic tumor amyloid (AODAM), galectin 7 amyloidosis (AGal), and Lect2 amyloidosis (ALECT2).

Selection, Synthesis, and Radiolabeling Peptides

Positively charged peptides shown in Table 3 were chemically synthesized and tested for in vivo and in vitro binding to amyloids. Some peptides were synthesized with an N-terminal CGGY (amino acids 1-4 of SEQ ID NO: 4) or GGGY (amino acids 1-4 of SEQ ID NO: 13) amino acid leader for ease of incorporating an agent for detection. Other peptides were synthesized with a second peptide at the N- or C-terminus. The second peptide may be cell penetrating peptide or a blood brain barrier translocating peptide. In the Examples, the terms "peptide" and "fusion peptide" are used interchangeably.

All peptides were analyzed by liquid chromatography-coupled mass spectrometry to confirm their sequence integrity, and determine the relative purity, using a C-18 reverse-phase matrix with acetonitrile:trifluoroacetic acid (ACN: TFA) as the mobile phase (Murphy, C. L. et al. (2006) Methods. Enzymol. 412, 48-52) and detection by UV spectroscopy ($A_{230}$). Preparations of peptides with less than 90% purity were enriched by bulk reverse-phase column chromatography.

Two methods of radiolabeling the peptides were employed. For radioiodination, the direct oxidative iodination of tyrosyl groups on the peptides was employed. This method yields product with high specific activity (~10-20 μCi/μg) of pure $^{125}$I-labeled peptide. The second method involves radiolabeling the peptides with $^{99m}$Tc according to the method of Tran et al. (Bioconjugate Chem, 2007, 18, 549-558). The quality of each radiolabeled peptide was assessed by SDS-PAGE (15% poly-acrylamide) analyzed with quantitative phosphor imaging.

Serum amyloid P component (SAP) is the gold standard amyloid imaging agent. Accordingly, radiolabeled SAP is used for comparison or control.

In Vivo Evaluation

Each of the radiolabeled peptides were evaluated for its specific reactivity with amyloids in vivo, using the TRIAD AA mouse model, by using SPECT imaging, biodistribution measurements, and autoradiography. The reactivity of the radiolabeled peptides were assessed in transgenic rapidly inducible amyloid disease (TRIAD) mice with systemic peripheral AA amyloidosis as well as control (amyloid free) mice, by imaging the mice. The reactivity of the peptides were evaluated at 1 hour, 2 hours, 4 hours, 8 hours, 12 hours, or 24 hours post injection of the radiolabeled peptides. The peptides identified as the best specific amyloid binding reagents from in vivo imaging studies using the TRIAD AA mouse model were p31 and peptides that were based on the structure of p31. The other peptides also bound amyloids, but not as well as these.

In a dual-energy imaging experiment, peptide p31 was labeled with Tc$^{99m}$ and SAP labeled with I$^{125}$ and the binding of each radiotracer was examined by using dual-energy microSPECT imaging in an individual TRIAD mouse with AA amyloidosis.

To examine the kinetics of the reactivity of peptides p48, p31, and p31-GGGY, dynamic PET imaging of I$^{124}$-labeled peptides p48, p31, p31-GGGY, and p50 (as a control) was performed in TRIAD mice with AA amyloidosis or wild type mice without amyloid. Finally, in a preliminary study, the binding of $I^{125}$-labeled SAP and $Tc^{99m}$-labeled peptide p31 was compared in the same TRIAD mouse with AA amyloidosis.

In Vitro Evaluation of Peptide Binding to Amyloids

The reactivity of biotinylated peptide p31 with amyloid deposits in formalin-fixed paraffin embedded tissues from patients with light chain (AL) amyloidosis, or Alzheimer's disease, and other forms of amyloidosis was examined. Consistent with in vivo imaging studies, peptide p31 bound tissue amyloid from these patients with great affinity.

Results

The immunohistochemical overlays of amyloid containing tissues show that the peptide p31 selectively bound to the amyloids in the tissue section as evidenced by the arrows which coincides with amyloid seen histologically in consecutive tissue sections (see FIGS. 1A-M)

Figure 4:
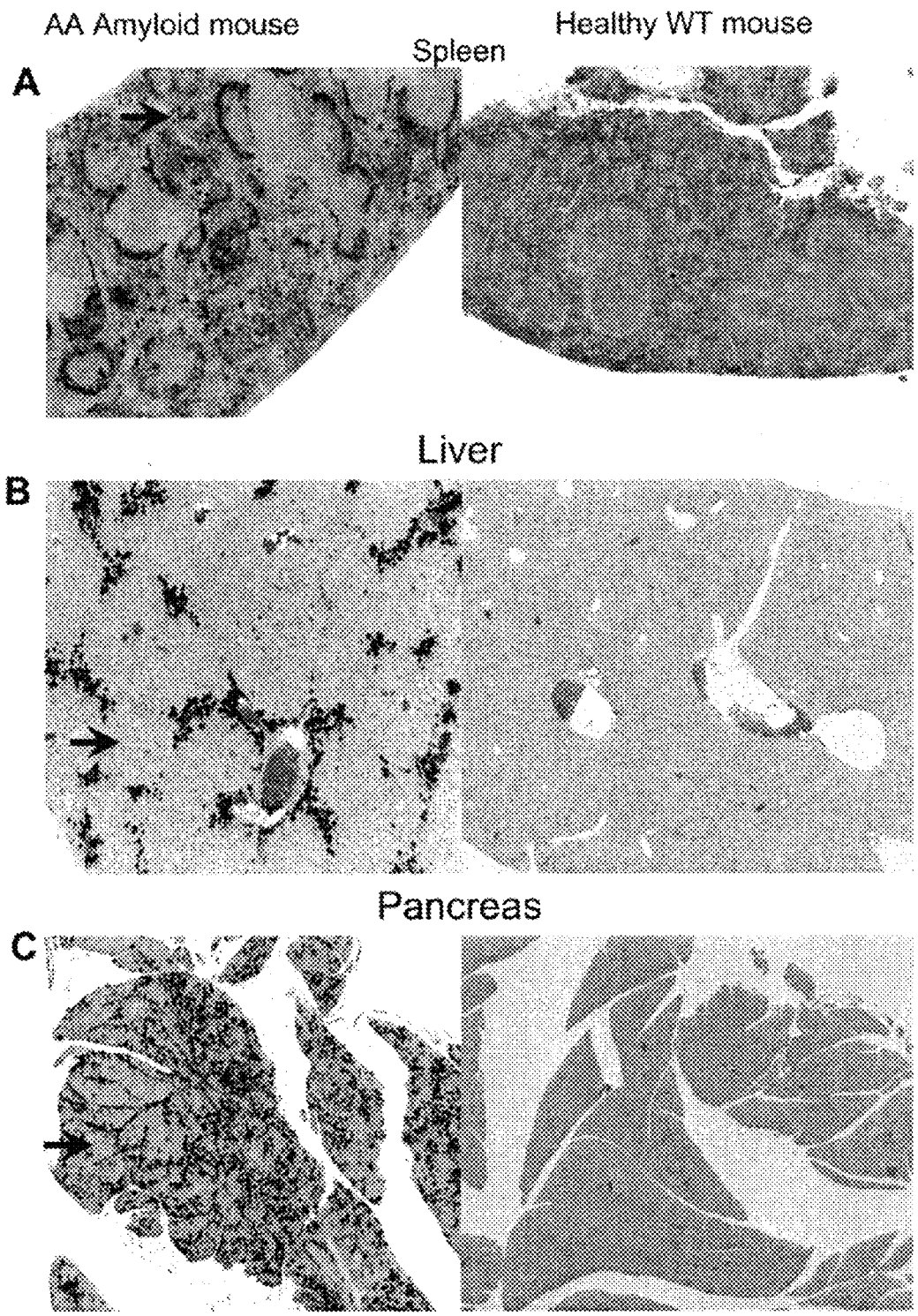
FIGS. 4A-F show $^{125}$I-labeled peptide p31 autoradiography. (A) Spleen of AA amyloid mouse and healthy mouse (WT); (B) Liver of AA amyloid mouse and healthy mouse; (C) Pancreas of AA amyloid mouse and healthy mouse; (D) Kidney of AA amyloid mouse; (E and F) Stomach and intestines of amyloid mouse and healthy mouse.
Figure 4:
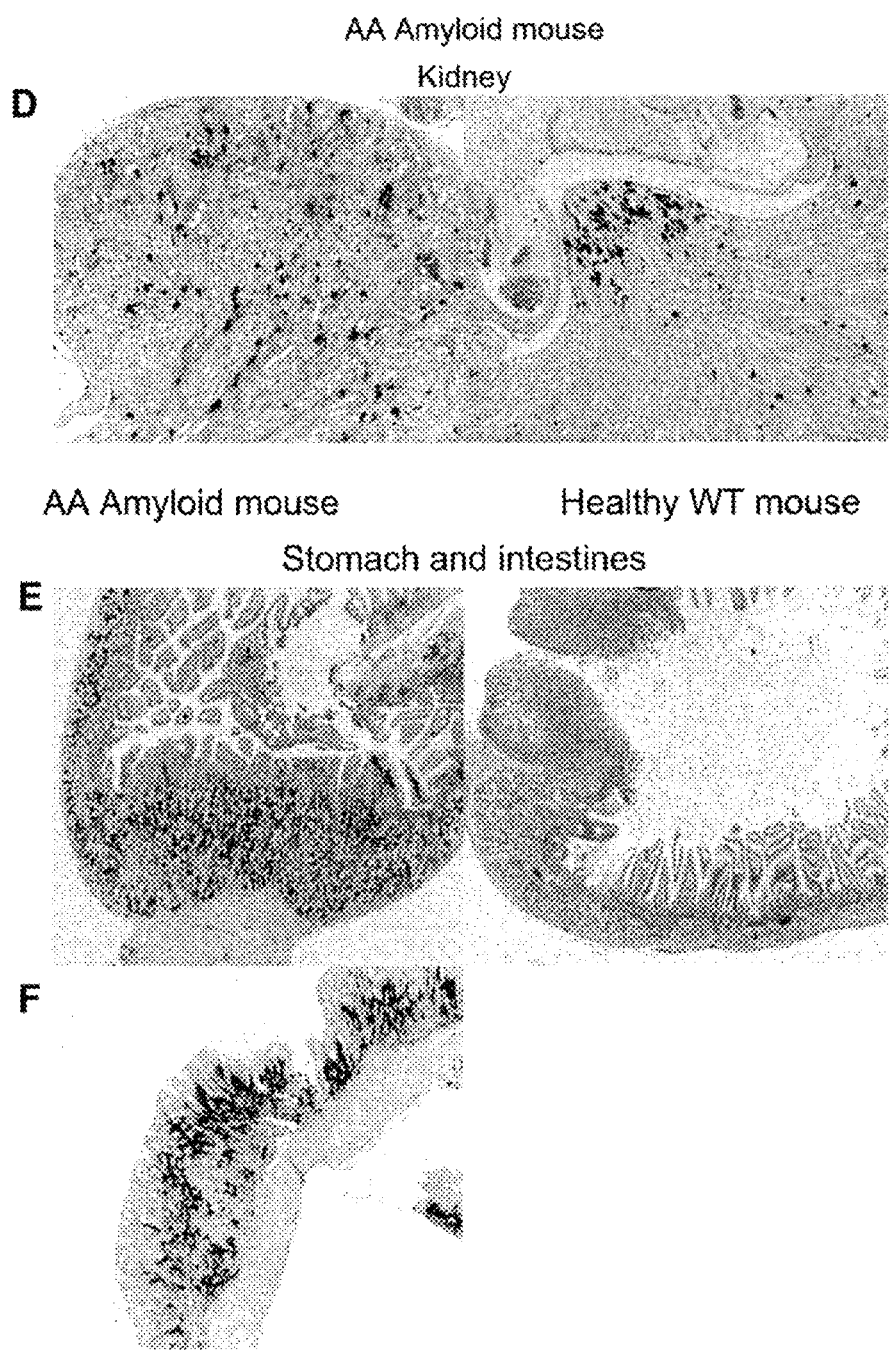

In vivo imaging of radiolabeled peptides demonstrated exquisite and intense co-localization of certain of the radiolabeled peptides with amyloid-continuing tissues in the mouse. (FIGS. 2 A and B and FIGS. 3A and B) More specifically, autoradiography (FIGS. 4 A-F) demonstrated the precise association of the peptides with amyloid deposits within the tissues (where black deposits represent the accumulation of radiolabeled peptide with amyloid).

Figure 5:
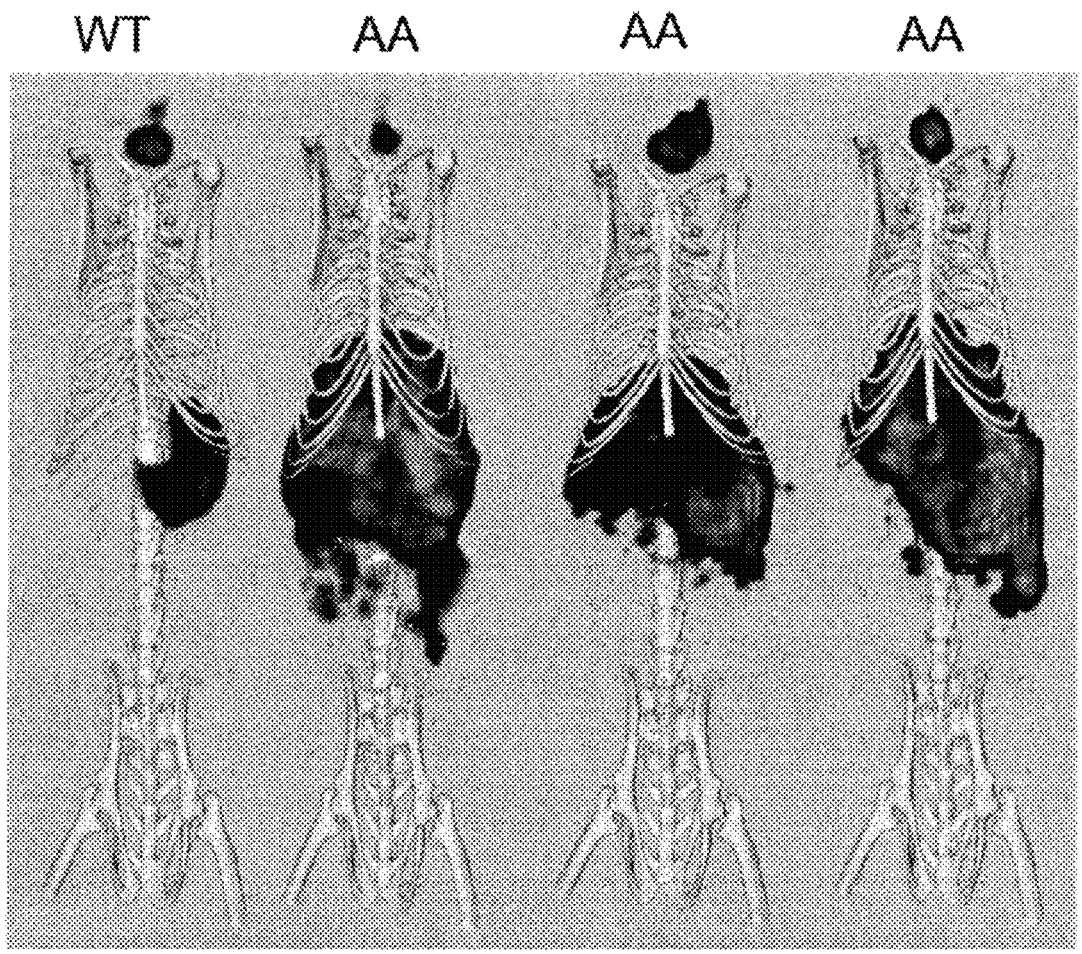
FIG. 5 shows $^{125}$I-labeled fusion p31 peptide SPECT imaging. Fusion peptides of p31 with either blood brain barrier translocating sequences (Wall1465) or cell penetrating peptides (Syb3 or Tat) were assessed for their ability to specifically image amyloid in vivo when radiolabeled with $^{125}$I. SPECT images were collected from WT (amyloid free) mice and those with visceral AA amyloidosis. The distribution of each of the fusion peptides in mice with AA differs significantly from that in WT mice. In the AA mice the peptides are retained by the amyloid deposits in the liver spleen and kidneys. These data indicate that the fusion peptides retain their amyloid-targeting properties in vivo.
Figure 6:
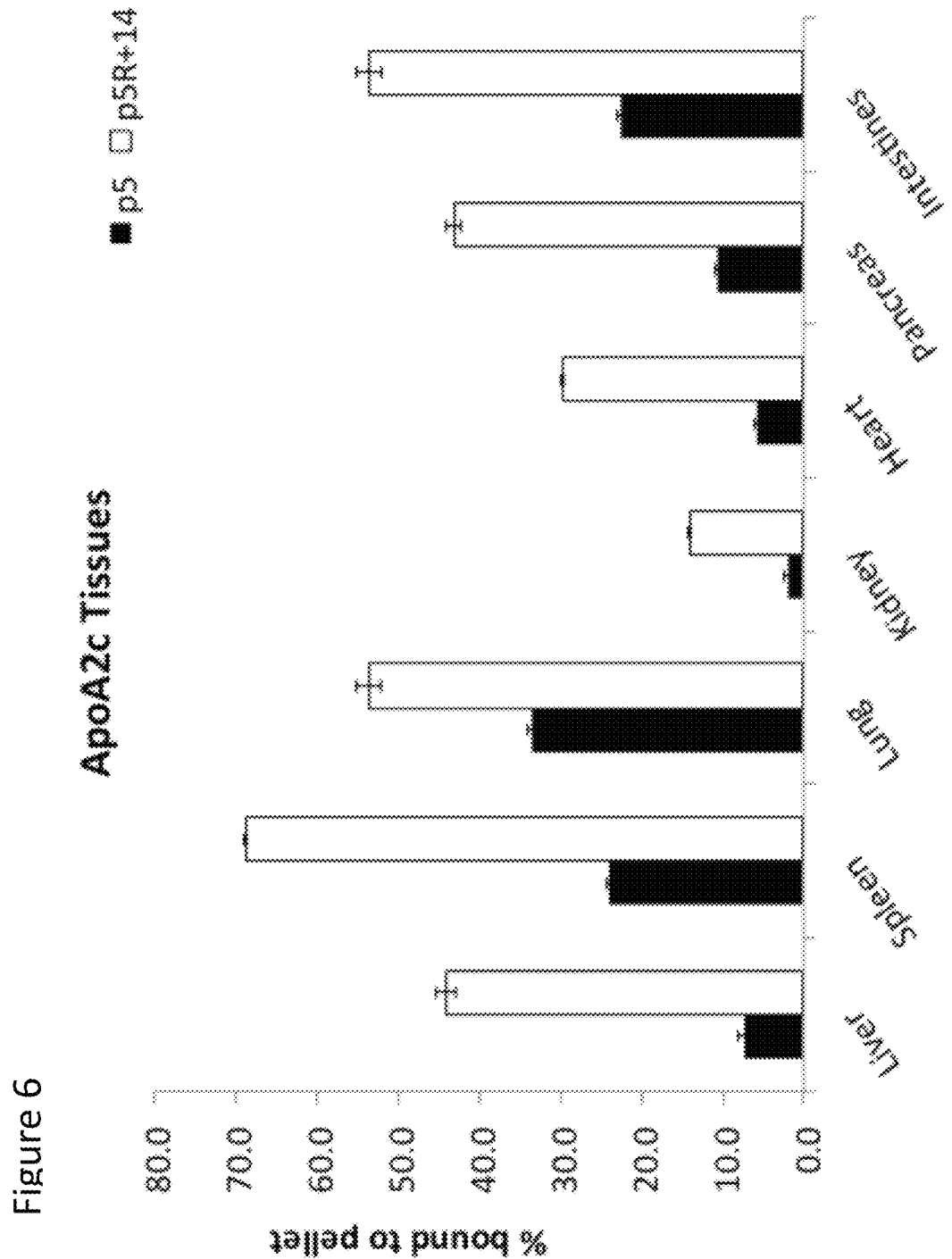
FIG. 6 shows the results of a peptide characterization and binding assay. The graph shows a comparison of binding abilities of both peptides. Note that p5R+14 exhibits higher binding in every tissue of interest from the ApoA2c-amyloid mouse. These data predict that p5R+14 would be a better imaging agent than p5 in this mouse model of amyloidosis.
Figure 7:
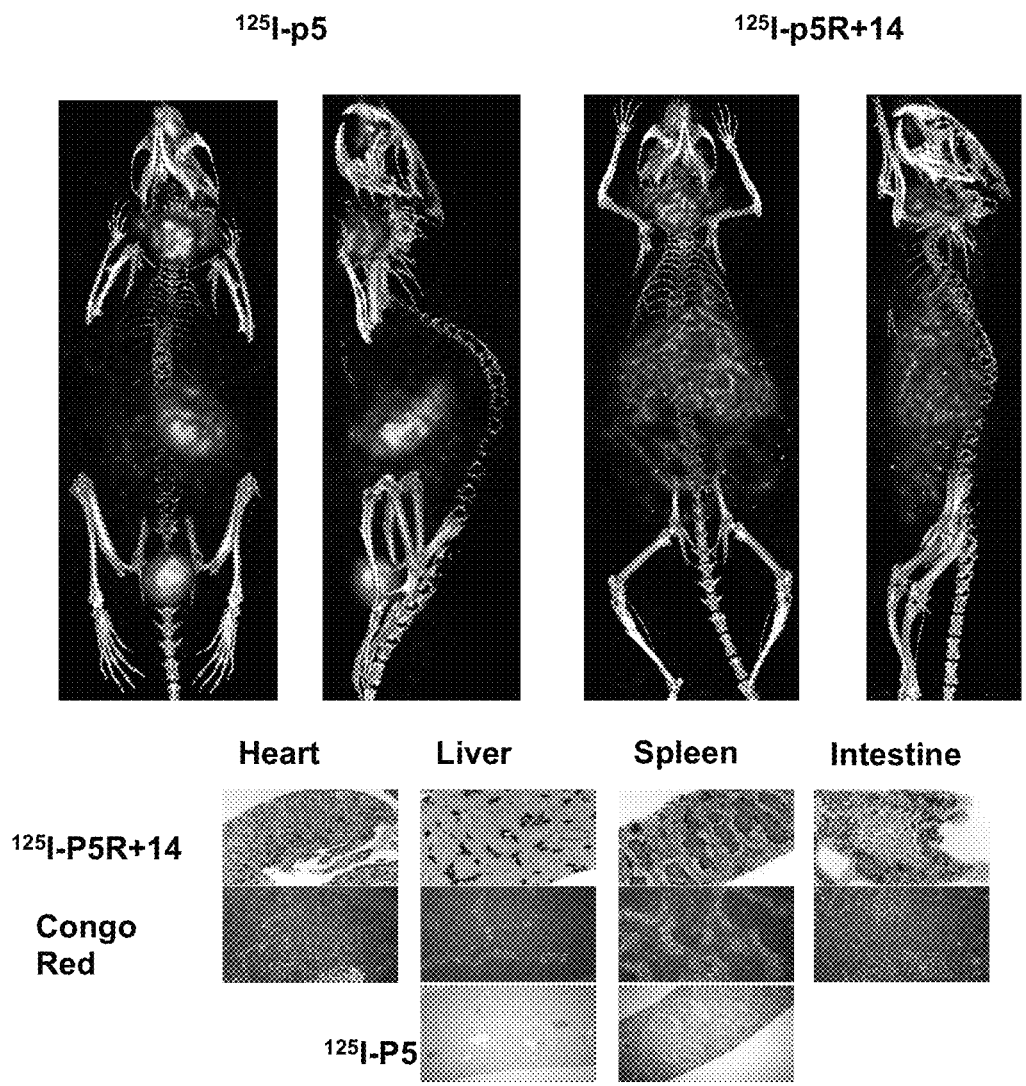
FIG. 7 shows In vivo studies of peptide distribution by using SPECT imaging and micro-autoradiography. Both sagital and coronal 3D SPECT/CT images show distinguishable differences between the uptake of peptide radiotracers in ApoA2c mice. Radioiodide is visible in the thyroid, stomach and bladder which is indicative of dehalogenation and clearance of the unbound peptide. In contrast, there is uptake of $^{125}$I-p5R+14 in amyloid-laden tissues such as the heart, liver, spleen and intestines. Micro-autoradiographs confirmed that the p5R+14 binding, represented as black deposits, is localized to amyloid within the tissues. The green birefringence seen in the Congo red slides shows patterns of amyloid deposition. The observed scant amounts of p5 in the tissues offers an explanation for the lack of positive amyloid uptake in the SPECT images.
Figure 8:
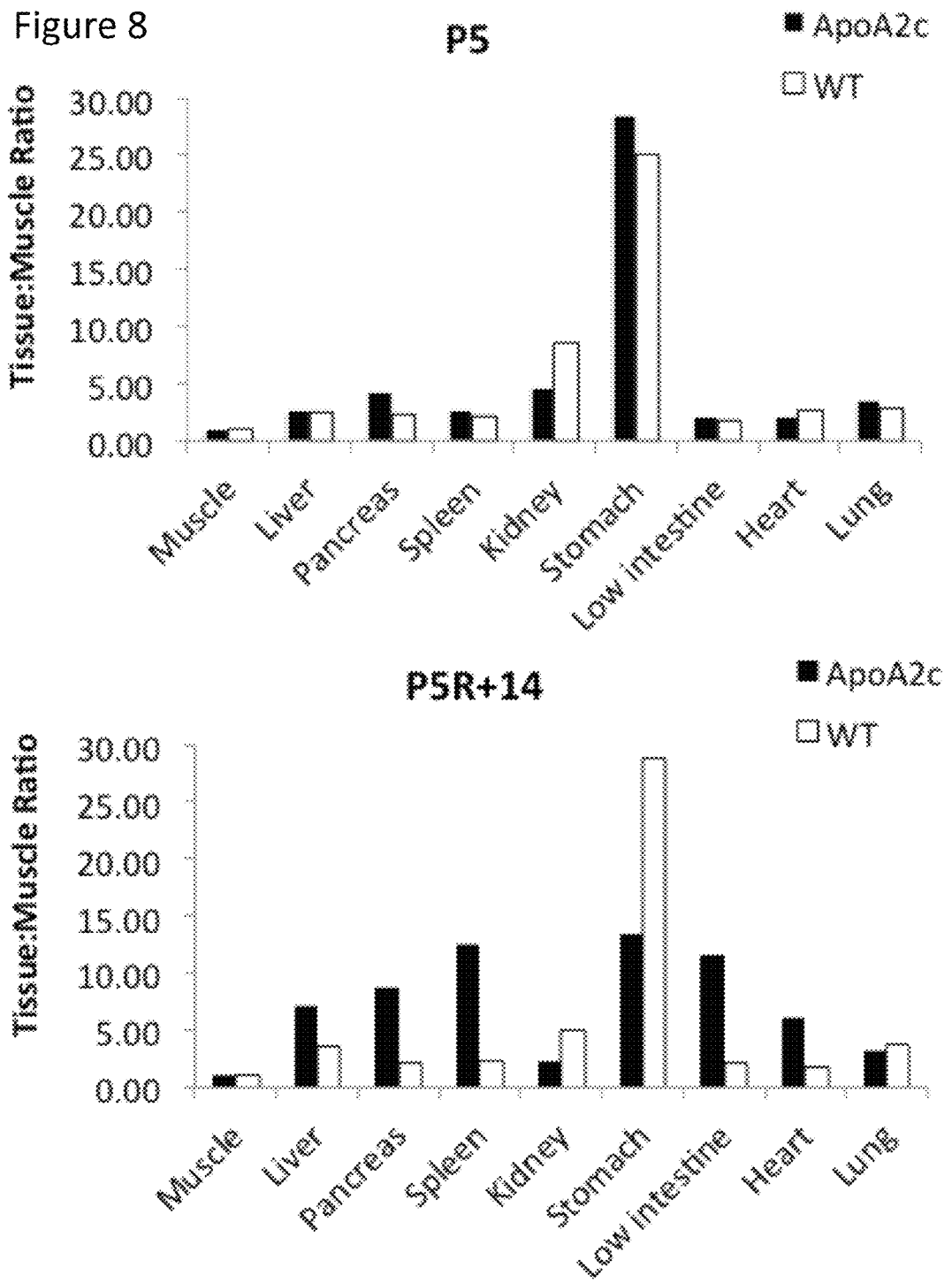
FIG. 8 shows the results of biodistribution measurements. The biodistribution of radiolabeled peptide are reported as a tissue-to-muscle ratios. The accumulation of p5 is not significantly higher in the ApoA2c mouse tissues as compared to healthy, WT, tissues. In contrast, there is clearly more p5R+14 binding to the diseased tissues.
Figure 9:
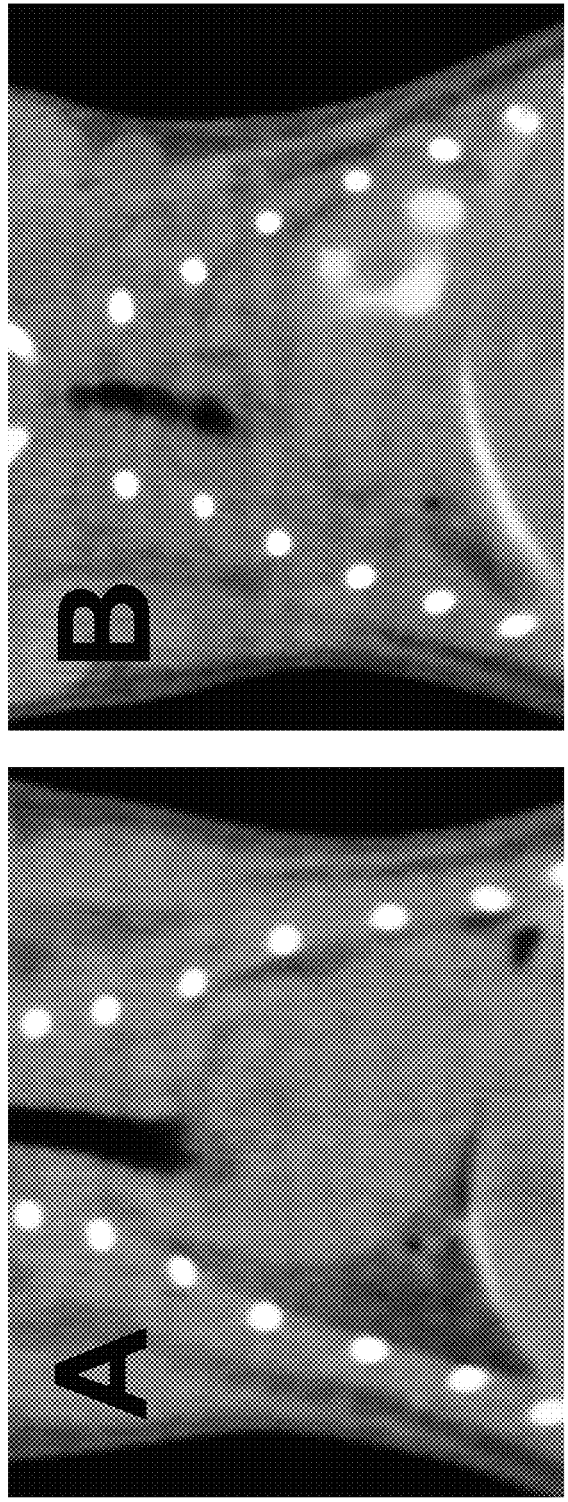
FIGS. 9A and 9B show two-dimensional SPECT/CT of chest cavity of WT (A) and ApoA2c (B) mice with $^{125}$I-p5R+14 radiotracer. The cardiac uptake is not part of blood pool clearance making this our first successful image of cardiac amyloid deposition.

$^{125}$I-labeled fusion p31 peptide SPECT imaging is shown in FIG. 5. Fusion peptides of p31 with either blood brain barrier translocating sequences (Wall1465) or cell penetrating peptides (Syb3 or Tat) were assessed for their ability to specifically image amyloid in vivo when radiolabeled with 125I. SPECT images were collected from WT (amyloid free) mice and those with visceral AA amyloidosis. The distribution of each of the fusion peptides in mice with AA differs significantly from that in WT mice. In the AA mice the peptides are retained by the amyloid deposits in the liver spleen and kidneys. These data indicate that the fusion peptides retain their amyloid-targeting properties in vivo.

Based on these data, peptide p31 and peptides that were based on the structure of p31 were identified as the best reagents for selective binding to AA amyloid in vivo and with remarkably good affinity. As an example, it has been shown that even at 24 h post-injection peptides p31 (and by way of a comparison, to a lesser degree p48) remained bound to the AA amyloid in vivo as evidenced in SPECT images and by biodistribution measurements. Moreover, it has been demonstrated by SPECT imaging that the p31 peptide is as effective as SAP for visualizing AA amyloid in the mouse, and would be comparable, if not better, in humans with amyloidosis FIGS. 3A and B). Biodistribution studies of p31 and SAP in mice suggest that p31 peptide binds more amyloid in vivo, likely because of its small size (Mw ~3 kD), which allows it to permeate through tissues as compared to the decameric SAP (Mw~250 kD). Autoradiographic data further indicate that p31 exhibits greater reactivity with murine pancreatic AA amyloid as compared to SAP and also binds AA amyloid in the necrotic renal papillae in vivo, which SAP does not.

To catalog the range of amyloids that p31 and other peptides may bind, biotinylated peptides using the biotinyl-maleimide adduct which interacts specifically with the solitary Cys residue in the "leader" sequence were prepared. The peptides were overlaid onto formalin-fixed 6 µm-thick amyloid-containing tissue sections, incubated overnight and then the distribution visualized using standard immunohistochemical techniques. This method shows that peptide p31 specifically binds significantly to the following amyloids:

| Amyloid | Precursor Protein |
|---|---|
| ALλ | λ light chains |
| ALκ | κ light chains |
| Aβ | Amyloid β peptide in Alzheimer's disease |
| ATTR | Transthyretin |
| AA (human and canine) | Serum amyloid protein A |
| AFibα | Fibrinogen α |
| AGal | Galectin 7 |
| ACEOT | ODAM |
| ALECT2 | Lectin2 |

In addition, the reactivity of the biotinyl-peptides to amyloid extract and synthetic amyloid fibrils using surface plasmon resonance and ELISA systems has been examined. The data confirm that certain of the peptides bind synthetic fibrils, notably those composed of human λ6 light chain variable domains derived from patients Wil and Jto.

Example 3

Peptide p31R

Design of Peptide p31R

Peptide p31R is a non-naturally occurring peptide. Peptide p31R was designed based on the amino acid sequence of peptide p31. It has been shown that when arginine replaces lysine in amphipathic alpha helices then these peptides have a greater propensity to form the helix and thus a greater propensity for ligand binding. Accordingly, peptide p31R was obtained by replacing lysine in the amino acid sequence of peptide p31 with arginine. The amino acid sequence of peptide p31R is

```
            (amino acids 5-31 of SEQ ID NO: 4)
    SRAQRAQARQARQAQRAQRAQARQARQ.
```

The oligomer CGGY was added to the amino terminus of p31R for ease of labeling the peptide. Accordingly, the fusion peptide p31R has the following amino acid sequence:

```
CGGYSRAQRAQARQARQAQRAQRAQARQARQ     (SEQ ID NO: 4)
```

Radiolabeling and In Vivo and In Vitro Evaluation of Peptide p31R

Peptide p31R was labeled in a similar manner as described above.

Peptide p31R was evaluated for its specific reactivity with amyloid in vivo, using the TRIAD AA mouse model, by using SPECT imaging, biodistribution measurements, and ARG, as described above.

Example 4

Visceral amyloidosis is a complex pathology comprising protein fibrils and numerous accessory molecules. Amyloid is associated with a myriad of diseases including type 2 diabetes and myeloma, but the US currently offers no method to effectively image this pathology in patients. To this end, we developed a peptide that preferentially binds to reactive (AA) amyloid deposits in vivo in a murine model. Our imaging studies with $^{125}$I-p5 now include a murine model of apolipoprotein AII (ApoA2c) amyloidosis. The peptide demonstrates a non-uniform pattern of amyloid reactivity in these animals; notably, there is no uptake of radiotracer in the splenic amyloid in vivo, and there is only slight uptake made visible by micro-autoradiography in other organs of interest.

The aim of this study was to further assess the reactivity of peptide p5 (also called p31-GGGY) with ApoA2c amyloid in vitro and to evaluate a novel peptide, p5R+14 (also called p31RGGGY+14), for imaging this type of amyloid.

The novel peptide, p5R+14, was radiolabeled with $^{125}$I via an oxidation reaction with chloramine T. The labeled peptide was separated from free iodide using size exclusion chromatography on a Sephadex G25 column. For ex vivo amyloid binding assays, the $^{125}$I-labeled p5 and p5R+14 peptides were added to 50 µL of homogenized tissue derived from wild type or amyloid laden ApoA2c mice. After a 1 h incubation, the amount of bound peptide (% of total) was assessed by gamma counting following centrifugation. For in vivo imaging, peptides p5 and p5R+14 were radiolabeled as above, and the radiopurities were determined by using SDS-PAGE and phosphor imaging.

Approximately 200 µCi was injected iv in the lateral tail vein of ApoA2c mice (n=3). SPECT/CT images were acquired using the Inveon Tri-Modality System at 2 or 4 h pi. Organs were harvested and biodistribution of radiotracers was determined and recorded as % injected dose/gram. For comparisons between the peptides, tissue to muscle ratios were used. The tissues were then fixed in formalin, paraffin embedded, sectioned and exposed to photographic emulsion for ~3 days.

Both peptide p5 and p5R+14 were able to bind to ApoA2c amyloid-laden tissues in the in vitro assay, but in general, peptide p5R+14 bound in greater amounts to all tissue samples as compared to p5 which indicates that it may prove to be a better imaging agent for this type of amyloid in vivo. SPECT imaging and biodistribution studies confirmed that p5R+14 bound cardiac amyloid deposits as well as those in the liver, spleen and intestines.

The in vitro amyloid-reactivity assay was used to demonstrate that the p5R+14 peptide was able to bind to deposits within amyloid-laden tissues better than the p5 peptide. Upon acquiring positive images in the ApoA2c mouse model, these studies indicate that the novel peptide, p5R+14, is a valuable tool for amyloid imaging as evidenced by its ability to bind to cardiac amyloid in addition to the other affected tissues.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

We claim:

1. A method of detecting amyloids in a subject, comprising:

contacting a tissue sample obtained from the subject, or administering to the subject, an isolated peptide that binds amyloids, wherein the peptide comprises an amino acid sequence of at least about 5 amino acids to at most about 55 amino acids and wherein the amino acid sequence comprises at least about 15% positively charged amino acids; and detecting the peptide bound to amyloids, thereby detecting the presence of amyloids in the tissue sample or in the subject, wherein the isolated peptide comprises the amino acid sequence as set forth is one of SEQ ID NO: 32 SEQ ID NO: 13 SEQ ID NO: 20 or SEQ ID NO: 22.

2. The method of claim 1, wherein the peptide is labeled with a detectable label.

3. The method of claim 2, wherein the detectable label is an imaging agent.

4. The method of claim 1, wherein detecting the presence of amyloids comprises imaging the tissue sample or the subject.

5. The method of claim 1, wherein the peptide is fused to a second peptide.

6. The method of claim 5, wherein the second peptide is an amino terminal or a carboxy terminal fusion peptide.

7. The method of claim 5, wherein the second peptide comprises the amino acid sequence CGGY (amino acids 1 to 4 of SEQ ID NO: 4) or GGGY (amino acids 1 to 4 of SEQ ID NO: 13).

8. A method of diagnosing amyloidosis in a subject, comprising:
    contacting a tissue sample obtained from the subject, or administering to the subject, an isolated peptide that binds amyloids, wherein the peptide comprises an amino acid sequence of at least about 5 amino acids to at most about 55 amino acids and wherein the amino acid sequence comprises at least about 15% positively charged amino acids; and
    detecting the peptide bound to amyloids, wherein the presence of amyloids indicates that the subject is suffering from amyloidosis, wherein the isolated peptide comprises the amino acid sequence as set forth is one of SEQ ID NO: 32 SEQ ID NO: 13 SEQ ID NO: 20 or SEQ ID NO: 22.

9. The method of claim 8, wherein the peptide is fused to a second peptide, wherein the second peptide comprises the amino acid sequence CGGY (amino acids 1 to 4 of SEQ ID NO: 4) or GGGY (amino acids 1 to 4 of SEQ ID NO: 13).

10. A method of monitoring progression of amyloidosis in a subject, comprising:
    contacting a tissue sample obtained from the subject, or administering to the subject, an isolated peptide that binds amyloids, wherein the peptide comprises an amino acid sequence of at least about 5 amino acids to at most about 55 amino acids and wherein the amino acid sequence comprises at least about 15% positively charged amino acids; and
    detecting the peptide bound to amyloids, thereby monitoring the progression of amyloidosis in the subject, wherein the isolated peptide comprises the amino acid sequence as set forth is one of SEQ ID NO: 32 SEQ ID NO: 13 SEQ ID NO: 20 or SEQ ID NO: 22.

11. The method of claim 10, wherein the peptide is fused to a second peptide, wherein the second peptide comprises the amino acid sequence CGGY (amino acids 1 to 4 of SEQ ID NO: 4) or GGGY (amino acids 1 to 4 of SEQ ID NO: 13).

12. A method of monitoring the response of a subject diagnosed with amyloidosis to a therapeutic agent, comprising:
    contacting a tissue sample obtained from the subject treated with the therapeutic agent, or administering to the subject treated with the therapeutic isolated peptide that binds amyloids, wherein the peptide comprises an amino acid sequence of at least about 5 amino acids to at most about 55 amino acids and wherein the amino acid sequence comprises at least about 15% positively charged amino acids; and
    detecting the peptide bound to amyloids, thereby monitoring the response of the subject to the therapeutic agent, wherein the isolated peptide comprises the amino acid sequence as set forth is one of SEQ ID NO: 32 SEQ ID NO: 13 SEQ ID NO: 20 or SEQ ID NO: 22.

13. The method of claim 12, wherein the peptide is fused to a second peptide, wherein the second peptide comprises the amino acid sequence CGGY (amino acids 1 to 4 of SEQ ID NO: 4) or GGGY (amino acids 1 to 4 of SEQ ID NO: 13).

14. A method of monitoring the efficacy of an anti-amyloid therapy in a subject, comprising:
    contacting a tissue sample obtained from the subject, or administering to the subject, an isolated peptide that binds amyloids, wherein the peptide comprises an amino acid sequence of at least about 5 amino acids to at most about 55 amino acids and wherein the amino acid sequence comprises at least about 15% positively charged amino acids; and
    detecting the peptide bound to amyloids, thereby monitoring the efficacy of the anti-amyloid therapy in the subject, wherein the isolated peptide comprises the amino acid sequence as set forth is one of SEQ ID NO: 32 SEQ ID NO: 13 SEQ ID NO: 20 or SEQ ID NO: 22.

15. The method of claim 14, wherein the peptide is fused to a second peptide, wherein the second peptide comprises the amino acid sequence CGGY (amino acids 1 to 4 of SEQ ID NO: 4) or GGGY (amino acids 1 to 4 of SEQ ID NO: 13).

* * * * *